United States Patent
Li

(10) Patent No.: US 6,762,330 B2
(45) Date of Patent: *Jul. 13, 2004

(54) CATALYSIS USING PHOSPHINE OXIDE AND SULFOXIDE COMPOUNDS

(75) Inventor: George Y. Li, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 241 days.

This patent is subject to a terminal disclaimer.

(21) Appl. No.: 09/900,353

(22) Filed: Jul. 6, 2001

(65) Prior Publication Data

US 2002/0137974 A1 Sep. 26, 2002

Related U.S. Application Data

(63) Continuation of application No. PCT/US00/18586, filed on Jul. 7, 2000.
(60) Provisional application No. 60/274,530, filed on Mar. 9, 2001.

(51) Int. Cl.⁷ .......................... C07C 41/18; C07C 2/02; C07C 211/45
(52) U.S. Cl. .................. 568/642; 568/643; 585/425; 585/427; 564/337
(58) Field of Search ................. 568/642, 643; 585/469, 400, 425, 427; 564/337

(56) References Cited

U.S. PATENT DOCUMENTS 5,756,804 A   5/1998  Haber
5,801,263 A   9/1998  Seitz
6,291,722 B1 * 9/2001  Li .......................... 568/642

OTHER PUBLICATIONS

Hartwig, John F., Palladium–Catalyzed Amination of Aryl Halides: Mechanism and Rational Catalyst Design, SYNLETT, 1997, 329–340, 4.
Suzuki, Akira, Recent Advances in the Cross–Coupling Reactions of Organoboron Derivatives with Organic Electrophiles, 1995–1998, Journal of Organometallic Chemistry, 1999, 147–168, 576.
Genet, Jean P., et al., Recent Developments of Palladium(0) Catalyzed Reactions in Aqueous Medium, Journal of Organometallic Chemistry, 1999, 305–317, 576.
Wolfe, John P., et al., A Highly Active Catalyst for the Room–Temperature Amination and Suzuki Coupling of Aryl Chlorides, Angewandte Chemie International Edition, 1999, 2413–2416, 38, No. 16, Wiley–VCH Verlag GmbH, Weinheim, Germany.
Hartwig, John F., et al., Room–Temperature Palladium–Catalyzed Amination of Aryl Bromides and Chlorides and Extended Scope of Aromatic C–N Bond Formation with a Commercial Ligand, Journal of Organic Chemistry, 1999, 5575–5580, 64, American Chemical Society, Easton, USA.

* cited by examiner

*Primary Examiner*—Rosalynd Keys
(74) *Attorney, Agent, or Firm*—Inna Y. Belopolsky

(57) ABSTRACT

Phosphine oxide and sulfoxide compounds were used with transition metals, preferably palladium and nickel, to produce biaryls, arylthiols, arylphosphine oxides and arylamines via cross-coupling reactions with aryl halides and arylboronic acids, aryl Grignard reagents, thiols, phosphine oxides or amines.

7 Claims, No Drawings

CATALYSIS USING PHOSPHINE OXIDE AND SULFOXIDE COMPOUNDS

CROSS REFERENCE TO RELATED APPLICATIONS

This application is a non-provisional of Provisional Application No. 60/274,530, filed Mar. 9, 2001. This application is also a continuation of International Application No. PCT/US00/18586, filed Jul. 7, 2000, which claims priority benefit of application Ser. No. 09/602,714, filed Jun. 26, 2000, now U.S. Pat. No. 6,291,722 which is a continuation-in-part of application Ser. No. 09/451,150, filed Nov. 30, 1999, now U.S. Pat. No. 6,124,462.

FIELD OF INVENTION

The invention relates to the use of phosphine oxide and sulfoxide compounds complexed with transition metals to produce biaryls and arylamines via cross-coupling reactions with aryl halides and arylboronic acids, aryl Grignard reagents, or amines.

BACKGROUND

Chelating phosphine compounds when bound to metal atoms are generally known to be useful as catalysts. One reaction which uses palladium phosphine catalysts is the coupling of aryl halides with amines for the production of arylamines, as reviewed by Hartwig, *SYNLETT*, 1997, (4), pg. 329–340. An example of this reaction is the coupling of chlorobenzene and piperidine to form N-phenylpiperidine:

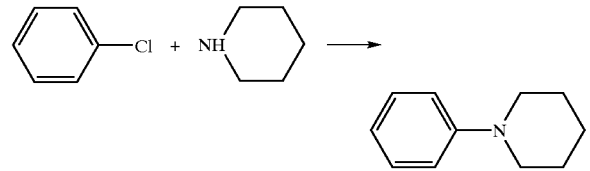

Another reaction in which palladium/phosphine catalysts have been used is the Suzuki reaction, where biaryls are produced through the coupling of arylboronic acids and aryl halides, as reviewed by Suzuki, A, *J. Orgmet. Chem.*, 576 (1999), pg. 147. One example of this reaction is the preparation of biphenyl from phenylboronic acid and chlorobenzene:

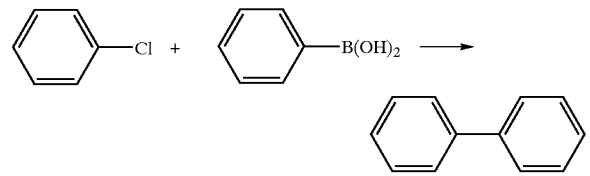

Both of these products are important classes of compounds widely used in the manufacture of pharmaceuticals, advanced materials, liquid polymers and ligands, and much work has been done on their preparation. However, there is an expanding need for stable, easily prepared catalysts that result in good yields and mild reaction conditions.

Preparation of new ligands has traditionally been performed one at a time after tedious synthesis and purification protocols. Combinatorial techniques have greatly accelerated the discovery of new ligands, but new synthetic schemes are needed. One valuable technique uses solid-phase supports. This solid-phase protocol allows reactions on a polymer-bound scaffold to be driven to completion by using large excesses of reagents in solution that can be easily filtered away from the polymer support. After the scaffold has been modified, an additional cleavage step then frees the small molecule from the polymer support into solution for isolation.

Phosphine oxide compounds and libraries have been prepared using polymer scaffolds in U.S. application Ser. No. 09/415,347 (U.S. Ser. No. 99/23509) which is incorporated in its entirety by reference. Lacking is a process for the convenient preparation of stable arylamines of the formula $R^1$—$NR^2R^3$ or biaryls of the formula $R^1$–$R^6$ using a stable phosphine catalyst under mild conditions and producing good yields.

SUMMARY OF THE INVENTION

This invention is directed to the use of phosphine oxide compounds complexed with transition metals to produce biaryls and arylamines, arylthiol, arylphosphine oxides and derivatives thereof, via cross-coupling reactions of aryl halides with arylboronic acids, arylmagnesium halides, amines, thiols, and phosphine oxides.

More specifically, the invention is directed twoards a process to prepare biaryls of the formula $R^1$–$R^7$ comprising contacting a Grignard reagent of the formula $R^7$—MgX with an aryl compound of the formula $R^1$—X in the presence of a catalytic amount of a coordination compound comprising one or more transition metals complexed to a phosphine oxide compound of the formula $HP(O)R^4R^5$, wherein X is a halogen; $R^1$ is an optionally substituted aryl; $R^7$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring.

Further, the invention includes a method for the use of phosphine oxides as ligands for homogeneous catalysis biaryls of the formula $R^1$–$R^7$ comprising: (1) preparing a coordination compound comprising one or more transition metals complexed to a phosphine oxide compound of the formula $HP(O)R^4R^5$, wherein X is a halogen; $R^1$ is an optionally substituted aryl; $R^7$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring; and 2) contacting a Grignard reagent of the formula $R^7$—Mgx with an aryl compound of the formula $R^1$—X in the presence of a catalytic amount of the coordination compound prepared in step (1) to form biaryls of the formula $R^1$-$R^7$.

The invention is also directed to a process to prepare biaryls of the formula $R^1$-$R^7$ comprising contacting a Grignard reagent of the formula $R^7$—Mgx with an aryl compound of the formula $R^1$—X in the presence of a catalytic amount of a coordination compound comprising one or more transition metals complexed to a phosphine sulfoxide compound of the formula $HP(S)R^4R^5$, wherein X is a halogen; $R^1$ is an optionally substituted aryl; $R^7$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring.

The invention is further directed to a process to prepare biaryls of the formula $R^1$–$R^6$ comprising contacting a boronic acid of the formula $R^6$—$B(OH)_2$ with an aryl compound of the formula $R^1$—X in the presence of a catalytic amount of a coordination compound selected from the group consisting of $\{[(t\text{-}Bu)_2P(OH)]_2PdCl]\}_2$, $[(t\text{-}Bu)_2P(OH)PdCl_2]_2$, and $[(t\text{-}Bu)_2P(Cl)PdCl_2]_2$, wherein X is a halogen; $R^1$ is an optionally substituted aryl; $R^6$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring.

The invention is also directed to a process to prepare biaryls of the formula $R^1$–$R^6$ comprising contacting a boronic acid of the formula $R^6$—$B(OH)_2$ with an aryl compound of the formula $R^1$—X in the presence of a catalytic amount of a coordination compound comprising one or more transition metals complexed to a phosphine oxide compound of the formula $HP(O)R^4R^5$, wherein X is a halogen; $R^1$ is selected from the group consisting of 3-methoxyphenyl, 2-methoxyphenyl, 4-thiomethoxyphenyl and phenyl; $R^6$ is phenyl; and $R^4$ and $R^5$ are t-butyl.

The invention is also directed to a process to prepare diaryl ketones of the formula $R^1$—C(=O)—$R^6$ comprising contacting a a boronic acid of the formula $R^6$—$B(OH)_2$ with a carbonate salt and an aryl compound of the formula $R^1$—X in the presence of a catalytic amount of a coordination compound comprising one or more transition metals complexed to a phosphine oxide compound of the formula $HP(O)R^4R^5$, wherein X is a halogen; $R^1$ is an optionally substituted aryl; $R^6$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring.

The invention is also directed towards a process to prepare biaryls of the formula $R^1$—S—$R^6$ comprising contacting a thiol of the formula $R^6$—SH with an aryl compound of the formula $R^1$—X in the presence of a catalytic amount of a coordination compound comprising one or more transition metals complexed to a compound of the formula $HP(S)R^4R^5$ or $HP(O)R^4R^5$, wherein X is a halogen; $R^1$ is an optionally substituted aryl; $R^6$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$, independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring.

The invention is also directed to a process to prepare biaryls of the formula $R^1$—$PR^{10}$—$R^6$ comprising contacting a compound of the formula $KPR^6R^{10}$ with an aryl compound of the formula $R^1$—X in the presence of a catalytic amount of a coordination compound comprising one or more transition metals complexed to a phosphine oxide compound of the formula $HP(O)R^4R^5$, wherein X is a halogen; $R^1$ is an optionally substituted aryl; $R^6$ is selected from the group consisting of hydrocarbyl, substituted hydrocarbyl, hydrocarbylamino, alkoxy, aryloxy, and heterocyclic; $R^{10}$ is selected from the group consisting of H and $R^6$; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring.

A process to prepare arylamines of the formula $R^1$—$NR^2R^3$ comprising contacting an amine of the formula $HNR^2R^3$ with an aryl compound of the formula $R^1$—X in the presence of a catalytic amount of a coordination compound of the formula $\{[(t\text{-}Bu)_2P(OH)]_2PdCl]\}_2$, $[(t\text{-}Bu)_2P(OH)PdCl_2]_2$, or $[(t\text{-}Bu)_2P(Cl)PdCl_2]_2$, wherein X is a halogen; $R^1$ is an optionally substituted aryl; and $R^2$ and $R^3$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^2$ and $R^3$ can together form a piperidyl ring.

The invention is also directed to a phosphine oxide transition metal complex dimer comprising two transition metal atoms bonded to at least one phosphine oxide ligand each, wherein each transition metal is bonded said ligands via metal-phosphorus bonds, and wherein the two transition metal atoms are bridged via two halogen atoms. Preferably, the phosphine oxide transition metal complex dimer comprises Formula I or Formula II or

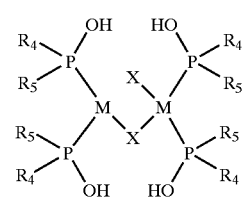

I

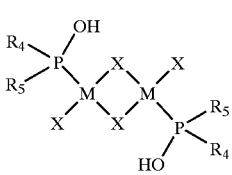

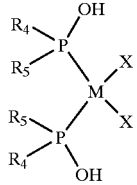

wherein M is a transition metal is selected from Periodic Group VIII; X is a halogen; $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring.

DETAILED DESCRIPTION OF THE INVENTION

This disclosure sets out methods for the use of phosphine oxide compounds complexed with transition metals to mediate carbon-carbon, carbon-heteroatom bond formations in the generation of biaryls, arylthiols, arylphosphines and arylamines via cross-coupling reactions with aryl halides and arylboronic acids, thiols, phosphine oxides or amines. Phosphine oxides were not previously used as ligands in homogeneous catalysis, primarily because the P-atoms do not have coordinated atoms with lone-pair electrons which were considered essential.

The processes of the instant invention are an improvement over similar processes in the art. The phosphine oxide compounds used in the instant processes are air-stable solids and are easily handled, and can be easily synthesized in a variety of forms using the methods described in U.S. patent application Ser. No. 09/415,347 (U.S. Ser. No. 99/23509). The processes are easily adapted to combinatorial procedures and can be used to construct libraries of biaryls and arylamines, which are themselves widely used in the manufacture of pharmaceuticals, advanced materials, liquid polymers and as ligands. Two examples of compounds or derivatives thereof that could be made by these processes are the synthetic dye Quinizarin Green and p-aminobiphenyl, used as an antioxidant.

Phosphine Oxide Compounds and Libraries

Phosphine oxide compounds of the formula $HP(O)R^4R^5$ are known to exist in two tautomeric forms:

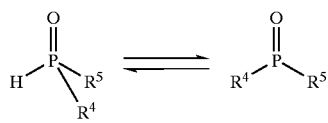

The phosphine oxide compounds can be prepared by any method. One such method is via the use of polymer scaffolds as described in U.S. application Ser. No. 09/415,347 (U.S. Ser. No. 99/23509), herein incorporated by reference. This scheme comprises the steps of contacting (i) a phosphine selected from the group consisting of $XPR^4R^5$ and $HP(=O)R^4R^5$, wherein X is a halogen, and $R^4$ and $R^5$ are independently selected from the group consisting of hydrocarbyl, substituted hydrocarbyl and heterocyclic, organometallic, Cl, Br, I, $SQ_1$, $OQ_2$, $PQ_3Q_4$ and $NQ_5Q_6$, when $Q_1$, $Q_2$, $Q_3$, $Q_4$, $Q_5$ and $Q_6$ are independently selected from the group consisting of hydrogen, hydrocarbyl, substituted hydrocarbyl, hydrocarbyl amino, alkoxy, aryloxy, and heterocyclic, and optionally $R^4$ and $R^5$ can together form a ring, with (ii) a solid support, resulting in at least one P in the phosphine attached indirectly or directly to the solid support via one or more covalent bonds, and optionally replacing one or more of $R^4$ and $R^5$ with any other $R^4$ and $R^5$ defined above. With this reaction scheme, $R^4$ and $R^5$ can be symmetric, unsymmetric, or chiral.

Virtually any solid material may be used as a support to prepare the phosphine oxide compounds provided it meets the following criteria:

The material is insoluble in organic, aqueous, or inorganic solvents. Organic polymer supports are acceptable in this regard but they generally need to be crosslinked. Inorganic support, such as metal oxides ($SiO_2$, $Al_2O_3$, $TiO_2$, $ZrO_2$, etc.), clays, and zeolites, and modified carbons are generally insoluble in these solvents and also may be used as supports.

The support contains reactive sites, which can be used for the covalent attachment of the phosphorus.

The reactive sites are isolated to prevent additional crosslinking during further chemical transformations.

The reactive sites are exposed to the reaction medium. With a polymer resin support this is achieved through the use of a resin which swells in a reaction solvent or is sufficiently porous to allow transport of the reaction medium through the polymer matrix.

The term solid support refers to a material having a rigid or semi-rigid surface that contains or can be derivatized to contain functionality, which covalently links a compound to the surface thereof. Other modifications may be made in order to achieve desired physical properties. Such materials are well known in the art and include, by way of example, polystyrene supports, polyacrylamide supports, polyethyleneglycol supports, metal oxides such as silica, and the like. Such supports will preferably take the form of small beads, pellets, disks, films, or other conventional forms, although other forms may be used.

A preferred solid support is an organic or inorganic polymer to which the phosphorus can be covalently attached through a side chain or pendant group of the polymeric backbone. The polymer may be crosslinked or modified. Suitable preferred polymers useful in the preparation of a supported phosphine compound or a combinatorial library of supported phosphine compounds includes polyolefins, polyacrylates, polymethacrylates, and copolymers thereof that meet the general criteria described above. A more preferred polymeric support is polystyrene wherein the phosphorus is attached to a pendant phenyl group on the polystyrene backbone. Most preferred is polystyrene, crosslinked with divinylbenzene. Specifically, polystyrenes commonly used for solid phase synthesis have been used. These particular resins are crosslinked with from 1 to 10 wt % divinylbenzene. The styrene moieties are substituted in the para or meta positions. Only a portion of the styrene moieties are substituted, typically resulting in functional group loadings of approximately 0.2 to 2.0 mmole per gram of resin, although this value may be higher or lower.

A combinatorial library of phosphine oxides can be used in the instant invention as well as single compounds. To create a library, one or more phosphines are reacted with one or more solid supports, generating a plurality of supported phosphine compounds. Alternatively, a library may be created by reacting one supported phosphine compound with a plurality of cleaving agents, as described below.

As used herein, a combinatorial library is an intentionally created collection of a plurality of differing molecules which can be prepared by selected synthetic means and screened for a desired activity or characteristic in a variety of formats (e.g., libraries of soluble molecules, libraries of compounds attached to resin beads, silica chips, or other solid supports). The libraries are generally prepared such that the compounds are in approximately equimolar quantities, and are prepared by combinatorial synthesis. Combinatorial synthesis refers to the parallel synthesis of diverse compounds by sequential additions of multiple choices of reagents which leads to the generation of large chemical libraries containing related molecules having molecular diversity. Screening methods for libraries vary greatly and are dependent upon a desired activity, the size of library, and the class of compounds in the library.

The libraries can be of any type. These types include but are not limited to arrays and mixtures. Arrays are libraries in which the individual compounds are simultaneously synthesized in spatially segregated locations, typically identified by their location on a grid. Mixture libraries contain a mixture of compounds that are simultaneously synthesized and assayed. Identification of the most active compound is then performed by any of several techniques well known in the combinatorial art, such as deconvolution. (*Proc. Natl. Acad. Sci. USA*, 91, pg. 10779 (1994)).

A preferred solid support for the combinatorial libraries of the instant invention is an organic or inorganic polymer as described above, to which the phosphorus can be covalently attached through a side chain or pendant group of the polymeric backbone.

One scheme used in attaching the P to the solid support is via the reaction of the halogen or hydrogen bonded to the phosphorus in the phosphine with a nucleophilic group that is covalently attached to a solid support. The term nucleophilic group is well recognized in the art and refers to chemical moieties having a reactive pair of electrons. This scheme can easily be adapted for combinatorial synthesis.

Examples of reactions to prepare the phosphine oxide compounds are shown but not limited to those in Scheme 1 below, where SS is the solid support, X is a halogen, M is any metal, R can be one or more of $R^4$ or $R^5$ as defined above, Z is a divalent attaching group covalently attached to at least one phosphorus in the phosphine, selected from the group consisting of hydrocarbylene, substituted hydrocarbylene, —O—, —S—, and —NR'—, where R' is selected from the group consisting of an optionally-substituted hydrocarbyl and halogen, and the Z, O, S, and N substituents are covalently attached to the solid support.

SCHEME I

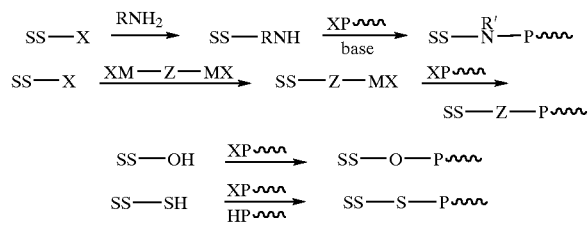

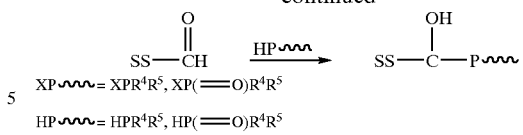

$XP\sim\sim = XPR^4R^5, XP(=\!\!=O)R^4R^5$ $HP\sim\sim = HPR^4R^5, HP(=\!\!=O)R^4R^5$ Any of the substituents in the above compounds may be replaced by other functional groups using any procedure known in the art. One or all of the substituents can be reacted in a single reaction, depending on the choice of reactants and reaction conditions. These reactions can easily be adapted for combinatorial processes. Examples of suitable procedures are shown by but not limited to those depicted in Scheme 2 below, where X, and M are as defined above, and R indicates any of $R^4$ or $R^5$, as defined above. Examples of suitable definitions for M include mg, Li, and Zn. Cp indicates a cyclopentadienyl ring.

SCHEME II

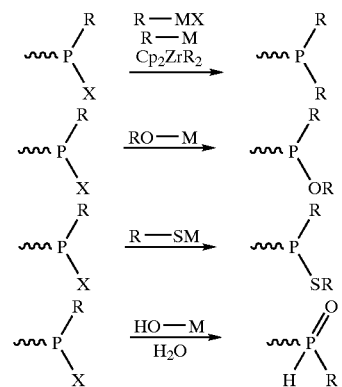

The phosphine oxide compounds are formed by cleaving the compound from the solid support by contacting the supported phosphine with a compound of the Formula ER", wherein E is an electrophilic group and R" is selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle. R" can be optionally replaced by any of $R^4$ or $R^5$. To create a library, one or more supported phosphines are reacted with one or more compounds of the Formula ER", generating a plurality of phosphine compounds.

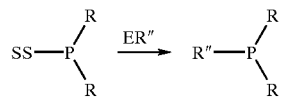

In the above process, E is any electrophilic group that will cleave the covalent bond attaching the phosphorus to the solid support. The term electrophilic group is a term well recognized in the art and refers to chemical moieties, which can accept a pair of electrons from a nucleophilic group as defined above. Suitable electrophilic groups include H, trimethylsilyl, $PCl_2$, halogens, and protons donated from compounds such as acids, alcohols, or amines.

In the instance where ER" is water, the resulting POH group would rearrange to yield to form the phosphine oxide compounds used in the instant invention. These compounds can also be formed from any other phosphine of the formula $RPR^4R^5$ via the replacement of R with an —OH group using any method known in the art. An equivalent rearrangement occurs when a PSH group is present.

Another method for preparing the phosphine oxide compounds is to prepare a phosphine oxide attached to the solid support, as explained above, then to cleave the phosphine oxide directly from the solid support.

After cleavage from the solid support, $R^4$ and $R^5$ may be replaced with any other substituent using any method known in the art, in order to prepare a further range of compounds, such as those described in *Encyclopedia of Inorganic Chemistry* (John Wiley & Sons, Vol. 6, pg. 3149–3213).

Reactions of Amines with Aryl Halides to Prepared Arylamines of the Formula $NHR^2R^3$ A process is described to prepare arylamines of the formula $R^1$—$NR^2R^3$ comprising contacting an amine of the formula $HNR^2R^3$ with an aryl compound of the formula $R^1$—X in the presence of a catalytic amount of a coordination compound comprising one or more transition metals complexed to a phosphine oxide compound of the formula $HP(O)R^4R^5$.

In this process, X is a halogen, $R^1$ is an optionally substituted aryl radical, $R^2$ and $R^3$ are independently selected from the group consisting of hydrogen, hydrocarbyl, substituted hydrocarbyl, hydrocarbylamino, alkoxy, aryloxy, and heterocyclic, and optionally $R^2$ and $R^3$ can together form a ring, and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$ and $NQ_5Q_6$, where $Q_1$, $Q_2$, $Q_3$, $Q_4$, $Q_5$ and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring. Optionally, the process can be performed intramolecularly; i.e. the amine functionality and the aryl functionality are both located on the same compound and the process results in a cyclization.

The amine and the aryl compound can be prepared by any method, including any of the well-known processes in the art.

"Coordination compound" refers to a compound formed by the union of a metal ion (usually a transition metal) with a non-metallic ion or molecule called a ligand or complexing agent.

The transition metals are defined as metals of atomic number 21 through 83. Preferably, the transition metal is from Periodic Group VIII (defined as Fe, Co, Ni, Ru, Rh, Pd, Os, Ir, and Pt). More preferred is Pd and Ni. The complex can be made by any synthetic method known in the art, either through direct reaction or via the use of a transition metal precursor.

The phosphine oxide compound is prepared as disclosed above. The phosphine oxide used in the instant invention can exist in either tautomeric form when present as a component of the complex. Examples of this include $\{[(t-Bu)_2P(OH)]PdCl_2]\}_2$, $\{[(t-Bu)_2P(OH)]_2PdCl]\}_2$, $\{[(Ph)_2P(OH)]_2PdCl]\}_2$ where Ph is phenyl, $[(Me_2CH)_2P(OH)]PdCl_2]_2$, $[(Cy)_2P(OH)]PdCl_2]_2$ where Cy is cyclohexyl. The complex can be isolated and purified before use, or be prepared and used in situ. The phosphine oxide may also be isolated and purified before use, or be prepared and used in situ. Many of these techniques are described in Hartley, F. R. (Ed), *Chem. Met.-Carbon Bond*, 1987, vol. 4, pp. 1163–1225).

By hydrocarbyl is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, cyclopentyl, methylcyclopentyl, cyclohexyl, methyl-cyclohexyl, benzyl, phenyl, o-tolyl, m-tolyl, p-tolyl, xylyl, vinyl, allyl, butenyl, cyclohexenyl, cyclooctenyl, cyclooctadienyl, and butynyl. Examples of substituted hydrocarbyl groups include methoxy, phenoxy, toluyl, chlorobenzyl, fluoroethyl, p—$CH_3$—S—$C_6H_5$, 2-methoxypropyl, and $(CH_3)_3SiCH_2$.

By aryl is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. By aryl is also meant heteroaryl groups where heteroaryl is defined as 5-, 6-, or 7-membered aromatic ring systems having at least one hetero atom selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl, which can optionally be substituted with, e.g., halogen, lower alkyl, lower alkoxy, lower alkylthio, trifluoromethyl, lower acyloxy, aryl, heteroaryl, and hydroxy.

A preferred process is where $R^1$ is an optionally substituted phenyl, $R^4$ and $R^5$ are independently selected from the group consisting of hydrocarbyl, substituted hydrocarbyl and heterocyclic, and where $R^2$ and $R^3$ are selected from the group consisting of hydrogen, optionally substituted aryl, and where $R^2$ and $R^3$ are hydrocarbyl and together form a ring. More preferred is where X is Cl, Br, or I, $R^1$ is selected from the group consisting of phenyl, 4-methylphenyl, 4-methoxyphenyl and 4-trifluoromethylphenyl, $R^2$ and $R^3$ are selected from the group consisting of hydrogen, phenyl, 4-methylphenyl, and together form a piperidyl ring, and $R^4$ and $R^5$ are selected from the group consisting of t-butyl, phenyl, i-propyl, and 2,4-methoxyphenyl and a piperidyl ring. Also preferably, the transition metal is from Periodic Group VIII. More preferred is Pd, or Ni, Reactions of Arylboronic Acids, Thiols, Phosphines with Aryl Halides to Prepare Biaryls of the Formula $R^1$-$R^6$, $R^1$—C(=O)—$R^6$, $R^1$—S—$R^6$, and $R^1$—$PR^{10}$—$R^6$.

The instant invention also describes a process to prepare biaryls of the formula $R^1$-$R^6$ comprising contacting a boronic acid of the formula $R^6$—$B(OH)_2$ with an aryl compound of the formula $R^1$—X in the presence of a catalytic amount of a coordination compound comprising one or more transition metals complexed to a phosphine oxide compound of the formula $HP(O)R^4R^5$; where X is a halogen, $R^1$ is an optionally substituted aryl, $R^6$ is selected from the group consisting of hydrocarbyl, substituted hydrocarbyl, hydrocarbylamino, alkoxy, aryloxy, and heterocyclic, and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring. Optionally, the process can be performed intramolecularly; i.e., the boronic acid functionality and the aryl functionality are both located on the same compound and the process results in a cyclization.

A preferred process is where $R^1$ is an optionally substituted phenyl, $R^4$ and $R^5$ are independently selected from the group consisting of hydrocarbyl, substituted hydrocarbyl and heterocyclic, and where $R^6$ is an optionally substituted aryl. More preferred is where X is Cl, Br, or I, $R^1$ is selected from the group consisting of of phenyl, 4-methoxyphenyl, 3-methoxyphenyl, 4-thiomethoxyphenyl, 2-methoxyphenyl and 4-methylphenyl; $R^6$ is selected from the group consisting of 4-methoxyphenyl, and phenyl; and $R^4$ and $R^5$ are selected from the group consisting of t-butyl, phenyl, i-propyl, and 2,4-methoxyphenyl. Also preferably, the transition metal is from Periodic Group VIII. More preferred is Pd and Ni. Also preferred is where the catalyst is $\{[(t-Bu)_2P(OH)]_2PdCl\}_2$, $[(t-Bu)_2P(OH)PdCl_2]_2$, or $[(t-Bu)_2P(Cl)PdCl_2]_2$. Most preferred is $\{[(t-BU)_2P(OH)]_2PdCl\}_2$.

When a carbonate salt is added to the reaction mixture, diaryl ketones of the formula $R^1$—(C=O)—$R^6$ are formed. A preferred process is where X is Cl or Br, $R^1$ is phenyl, $R^6$ is phenyl, and $R^4$ and $R^5$ are t-butyl. Also preferably, the catalyst is $\{[(t-Bu)_2P(OH)]_2PdCl\}_2$. The carbonate salt can be any salt that is a source of carbonate ($CO_3^{-2}$) ions, preferably a alkali or alkaline earth salt such as $K_2CO_3$.

The instant invention also describes a process to prepare biaryls of the formula $R^1$—S—$R^6$ comprising contacting a thiol of the formula $R^6$—SH with an aryl compound of the formula $R^1$—X in the presence of a catalytic amount of a coordination compound comprising one or more transition metals complexed to a phosphine sulfoxide compound of the formula $HP(S)R^4R^5$ or a phosphine oxide compound of the formula $HP(O)R^4R^5$. $R^1$, $R^6$, $R^4$ and $R^5$ and the phosphine sulfoxides and oxides are as described above. Optionally, the process can be performed intramolecularly; i.e., the thiol functionality and the aryl functionality are both located on the same compound and the process results in a cyclization. A preferred process is where $R^1$ is an optionally substituted phenyl, $R^4$ and $R^5$ are independently selected from the group consisting of hydrocarbyl, substituted hydrocarbyl and heterocyclic, and where $R^6$ is an optionally substituted aryl. More preferred is where X is Cl, Br, or I, $R^1$ is phenyl, $R^6$ is t-butyl or phenyl, and $R^4$ and $R^5$ are t-butyl. Also preferably, the transition metal is from Periodic Group VIII. More preferred is Pd or Ni. More preferred also is where the catalyst is $\{[(t-Bu)_2P(OH)]_2PdCl\}_2$.

Also described is process to prepare biaryls of the formula $R^1$—$PR^{10}$—$R^6$ comprising contacting a compound of the formula $KPR^7R^{10}$ with an aryl compound of the formula $R^1$—X in the presence of a catalytic amount of a coordination compound comprising one or more transition metals complexed to a phosphine oxide compound of the formula $HP(O)R^4R^5$. $R^1$, $R^6$, $R^4$ and $R^5$ and the phosphine oxides are as described above, and $R^{10}$ is selected from the group consisting of H and $R^6$. Optionally, the process can be performed intramolecularly; i.e., the phospine functionality and the aryl functionality are both located on the same compound and the process results in a cyclization. A preferred process is where $R^1$ is an optionally substituted phenyl, $R^4$ and $R^5$ are independently selected from the group consisting of hydrocarbyl, substituted hydrocarbyl and heterocyclic, and where $R^{10}$ is $R^6$, and $R^6$ are an optionally substituted aryl. More preferred is where X is Cl, and the catalyst is $\{[R^4R^5 P(OH)]_2PdCl\}_2$, $R^1$ is 4-tolyl or 2-methoxyphenyl, $R^6$ is phenyl, and $R^4$ and $R^5$ are t-butyl. Also preferably, the transition metal is from Periodic Group VIII. More preferred is Pd.

Reactions of Aryl Grignards with Aryl Halides to Prepare Biaryls of the Formula $R^1$–$R^6$ The instant invention also describes a process to prepare biaryls of the formula $R^1$–$R^7$ comprising contacting a Grignard reagent of the formula $R^7$—MgX with an aryl compound of the formula $R^1$—X in the presence of a catalytic amount of a coordination compound comprising one or more transition metals complexed to a phosphine oxide compound of the formula $HP(O)R^4R^5$; where X is a halogen, $R^1$ is an optionally substituted aryl, $R^7$ is selected from the group consisting of hydrocarbyl, substituted hydrocarbyl, hydrocarbylamino, alkoxy, aryloxy, and heterocyclic, and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring. Optionally, the process can be performed intramolecularly; i.e., the Grignard functionality and the aryl functionality are both located on the same compound and the process results in a cyclization.

A preferred process is where $R^1$ is an optionally substituted phenyl, $R^4$ and $R^5$ are independently selected from the group consisting of hydrocarbyl, substituted hydrocarbyl and heterocyclic, and where $R^7$ is an optionally substituted aryl. More preferred is where X is Cl, $R^1$ is selected from the group consisting of 4-methoxylphenyl and phenyl, $R^7$ is o-tolyl, and $R^4$ and $R^5$ are t-butyl. Also preferably, the transition metal is from Periodic Group VIII. More preferred is Ni.

The process described above to produce biaryls of the formula $R^1$–$R^7$ comprising contacting a Grignard reagent of the formula $R^7$—MgX with an aryl compound of the formula $R^1$—X may also be performed in the presence of a catalytic amount of a coordination compound comprising one or more transition metals complexed to a phosphine sulfoxide of the formula $HP(S)R^4R^5$. $R^1$, $R^7$, $R^4$ and $R^5$ are as described above. Optionally, the process can be performed intramolecularly; i.e., the Grignard functionality and the aryl functionality are both located on the same compound and the process results in a cyclization. The phosphine sulfoxides can be prepared using the procedures described above for the phosphine oxides. The phosphine sulfoxide used in the instant invention can also exist in either tautomeric form when present as a component of the complex. The complex can be isolated and purified before use, or be prepared and used in situ. The phosphine sulfoxide may also be isolated and purified before use, or be prepared and used in situ. A preferred process is where $R^1$ is an optionally substituted phenyl, $R^4$ and $R^5$ are independently selected from the group consisting of hydrocarbyl, substituted hydrocarbyl and heterocyclic, and where $R^7$ is an optionally substituted aryl. More preferred is where X is Cl, Br, or I. $R^1$ is selected from the group consisting of 4-methoxylphenyl and phenyl, $R^7$ is o-tolyl, and $R^4$ and $R^5$ are t-butyl. Also preferably, the transition metal is from Periodic Group VIII. More preferred is Ni.

Schemes 1 and 2 to form phosphine oxides and sulfoxides, the cleaving procedures, and the coupling reactions disclosed above are preferably performed under dry, inert atmosphere with dry, deoxygenated solvents. Any solvent is suitable provided that it is inert to all reagents and products. Suitable temperatures for homogeneous catalysis range from −80° C. to 200° C. Preferred temperatures are about 0° C. to about 150° C. Preferably a base should be added in the coupling reactions disclosed. Preferred bases are CsF, $CsCO_3$, $K_2CO_3$, Na2CO3 and NaOtBu.

The following non-limiting Examples are meant to illustrate the invention but are not intended to limit it in any way.

Materials and Methods

All manipulations of air-sensitive materials were carried out with rigorous exclusion of oxygen and moisture in flame-dried Schlenk-type glassware on a dual manifold Schlenk line, interfaced to a high-vacuum ($10^{-4}$–$10^{-5}$ Torr) line, or in a nitrogen-filled Vacuum Atmospheres glovebox with a high-capacity recirculator (1–2 ppm of $O_2$). Before use, all solvents were distilled under dry nitrogen over appropriate drying agents (such as sodium benzophenone ketyl and metal hydrides except for chlorinated solvents). Deuterium oxide, THF-$D_8$, $C_6D_6$ and chloroform-d were purchased from Cambridge Isotopes (Andover, Mass.). All organic and inorganic starting materials were purchased from Aldrich Chemical Co. (Milwaukee Wis.), Farchan Laboratories Inc. (Gainesville, Fla.), Strem Chemicals (Newburyport, Mass.), Calbiochem—NovaBiochem Corp. (San Diego, Calif.), Rieke Metals, Inc. (Lincoln, Nebr.), or Lancaster Synthesis Inc. (Windham, N.H.), and when appropriate were distilled prior to use.

| List of abbreviations | |
|---|---|
| dba | Bis(dibenzylideneacetone) |
| DVB | Divinylbenzene |
| GC/MS | Gas chromatography/mass spectroscopy |
| FT | Fourier transform |
| h | Hour |
| i.d | Inner diameter |
| in. | Inch |
| Me | Methyl |
| mg | milligram |
| NMR | Nuclear magnetic resonance |
| tBu | tert-butyl |

Physical and Analytical Measurements

NMR spectra were recorded on either a Nicolet NMC-300 wide-bore (FT, 300 MHz, $^1$H; 75 MHz, $^{13}$C, 121 MHz $^{31}$P), or GE QM-300 narrow-bore (FT, 300 MHz, $^1$H) instrument. Chemical shifts ($\delta$) for $^1$H, $^{13}$C are referenced to internal solvent resonances and reported relative to $SiMe_4$. $^{31}$P NMR shifts are reported relative to external phosphoric acid. Analytical gas chromatography was performed on a Varian Model 3700 gas chromatograph with FID detectors and a Hewlett-Packard 3390A digital recorder/integrator using a 0.125 in. i.d. column with 3.8% w/w SE-30 liquid phase on Chromosorb W support. GC/MS studies were conducted on a VG 70-250 SE instrument with 70 eV electron impact ionization.

The polymer bound monophosphines were prepared as described in U.S. patent application Ser. No. 09/415,347 (U.S. Ser. No. 99/23509). The functional groups on the phosphines can be added in two steps to yield unsymmetrical substitutions, or in one step to yield more symmetrical substitution.

A solution of t-butylamine (276 g, 3.78 moles) and KI (0.3 g, 2 mmol) in 1000 mL of THF was treated with chloromethylpolystyrene-divinylbenzene (Merrifield resin, 2% DVB, 75 g, 1.26 mmol/g, 94.5 mmol) while stirring at room temperature for 30 min. The suspension was then refluxed for 24 h before the solution was filtered off. The resulting resin was washed with $H_2O$ (3×250 mL), THF (3×150 mL), then hexane (3×200 mL). After drying in vacuum overnight, 75 g of the resin were obtained (98% yield according to N elemental analysis. Anal. calculated for polymer-NHC(Me)$_3$: N, 1.25. Found: N, 1.22). Also the disappearance of $^1$H resonances of polymer-Ph—$CH_2$—Cl ($CH_2$=~4.5 ppm) and the appearance of $^1$H resonances of polymer-Ph—$CH_2$—NHC(Me)$_3$ ($CH_2$=~3.7 ppm) indicates that the chloromethyl groups were completely transformed to tert-butylaminometyl groups. Hereafter this will be referred to as Resin I.

A solution of $PCl_3$ (26 g, 189 mmol) in 400 mL of THF was treated slowly with Resin I from above (25 g, 1.21 mmol/g, 30.3 mmol) while stirring at room temperature for a period of 30 min. before $Et_3N$ (16 g, 157.5 mmol) was added. The resulting suspension was stirred at room temperature overnight before the solution was filtered off. The resin was washed with hexane (2×50 mL), $CH_2Cl_2$ (5×80 mL), and hexane (5×30 mL). The resulting polymer-bound $PCl_2$ resin was dried in vacuum overnight. $^{31}$P NMR (122 MHz, $CDCl_3$): $\delta$179.1 ppm.

A suspension of the polymer-bound $PCl_2$ resin from above (5.0 g, 1.12 mmol/g, 5.6 mmol) in 150 mL of THF was treated slowly with phenylmagnesium bromide (2 M solution in diethylether, 64 mmol). The resulting mixture was stirred at room temperature for 30 min. before the solution was filtered off and the resin was washed with THF (3×50 mL), $Me_2CHOH$/THF (20% $Me_2CHOH$, 10 mL), hexane (3×30 mL). The resulting resin was dried in vacuum overnight to yield polymer-bound $PPh_2$. $^{31}$P NMR (122 MHz, $CDCl_3$): $\delta$52.3 ppm.

A solution of $Cl_2PPh$ (33.8 g, 189 mmol) and $Et_3N$ (16.0 g, 157.5 mmol) in 500 mL of THF was treated slowly with Resin I (25.0 g, 1.21 mmol/g, 30.3 mmol) while stirring at room temperature for a period of 10 min. The resulting suspension was stirred at room temperature overnight before the solution was filtered off. The resin was washed with THF (50 mL), hexane (3×50 mL), $CH_2Cl_2$ (4×50 mL), and hexane (2×50 mL). The resulting polymer-bound PPhCl resin was dried in vacuum overnight. $^{31}$P NMR (122 MHz, $CDCl_3$): $\delta$135.4 ppm.

A suspension of the resulting resin, the polymer-bound PPhCl, (5.0 g, 1.03 mmol/g, 5.2 mmol) in 150 mL of THF was treated slowly with i-propylmagnesium chloride (0.5 M solution in diethylether, 32.0 mmol). The resulting mixture was stirred at room temperature for 2 h before the solution was filtered off and the resin was washed with THF (3×10 mL), $Me_2CHOH$/THF (20% $Me_2CHOH$, 5 mL), hexane (3×30 mL). The resulting resin was dried in vacuum overnight to afford polymer-bound (i-$C_3H_7$)PPh. $^{31}$P NMR (122 MHz, $CDCl_3$): $\delta$655.5 ppm.

The following Experiments illustrate the preparation of the phosphine oxide catalyst used in the method.

Experiment 1

Synthesis of ($Me_2CH$)PH(O)(Ph)

A suspension of polymer-bound PPh(CHMe$_2$) prepared as described above (1.25 g, 1.02 mmol/g, 1.28 mmol, $^{31}$P NMR (121 MHz, $CDCl_3$): $\delta$55.5 ppm) and $H_2O$ (0.1 g, 4.8 mmol) in THF (10 mL) was refluxed overnight before the resin was filtered off and washed with THF (2×5 mL). The filtrate was dried under vacuum to remove the solvent and excess $H_2O$. The resulting residue was 80 mg (37% yield) of ($Me_2CH$)PH(O)(Ph). It was >95% pure by $^1$H NMR and GC/MS. $^{31}$P NMR (121 MHz, $CDCl_3$, $^1$H-decoupled): $\delta$47.8. $^{31}$P NMR (121 MHz, $CDCl_3$, $^1$H-coupled): $\delta$47.8 (d, $J_{p-H}$=487.7 Hz). $^1$H NMR (500 MHz, $CDCl_3$): $\delta$7.74–7.53 (m, 5H), 7.25 (d, $J_{p-H}$=487.5 Hz, 1H), 2.33 (m, 1H), 1.12 (m, 6H). $^{13}$C NMR (125 MHz, $CDCl_3$): $\delta$133.8, 131.1, 129.4, 125.4, 28.0, 14.7. HRMS: Calculated for $C_9H_{13}PO(M^+)$: 168.0704. Found: 168.0704.

Experiment 2

Synthesis of (Me$_3$C)PH(O)(CMe$_3$)

A solution of (Me$_3$C)$_2$PCl (3.0 g, 16.6 mmol, Aldrich) in 5.0 mL of CH$_2$Cl$_2$ was treated with H$_2$O (0.5 g, 27.8 mmol) over a period of 5 min. The resulting reaction mixture was stirred at room temperature for an additional 30 min. Removal of solvent and excess H$_2$O afforded 2.45 g (91% yield) of (Me$_3$C)PH(O)(CMe$_3$). It was >95% pure by $^1$H NMR and GC/MS. The pure product was obtained by sublimation (ca. 130° C./10$^{-3}$ torr), $^{31}$P NMR (121 MHz, CDCl$_3$, $^1$H-decoupled): δ69.8 ppm. $^{31}$P NMR (121 MHz, CDCl$_3$, $^1$H-coupled): δ69.8 (d, J$_{P-H}$=434.2 Hz). $^1$H NMR (500 MHz, CDCl$_3$): δ5.96 (d, J$_{P-H}$=434.7 H $^1$H), 1.14 (d, H$_{P-H}$=156.4 Hz, 18H). $^{13}$C NMR (125 MHz, CDCl$_3$): δ33.8 ppm 14 (d, H$_{P-C}$=58.0 Hz), 25.6 ppm. MS: Calculated for C$_8$H$_{19}$PO(M$^+$): 162.1. Found: 163.4 (M$^+$+H).

Experiment 3

Synthesis of 2-PH(O)(i-Pr)-1, 5-(MeO)$_2$C$_6$H$_3$

A solution of PBr$_3$ (2.5 g, 9.2 mm) in 15 mL of pyridine was treated with 1,3-dimethoxybenzene (2.5 g, 18.1 mm) over a period of 5 min. The resulting mixture was then refluxed for 4 h to give the crude 1-dibromophosphino-2,4-dimethoxybenzene ($^{31}$P NMR: δ159.2 ppm). This compound was used directly for the next step without further purification. Next, polymer-supported secondary amines (10.0 g, 1.1 mmol/g, 11.0 mmol) was slowly added into the mixture above while stirring at room temperature for a period of 10 min. The resulting suspension was stirred at room temperature overnight before the solution was filtered off. The resin was washed with THF (50 mL), hexane (3×50 mL), CH$_2$Cl$_2$ (4×50 mL), and hexane (2×50 mL). The resulting resin was dried in vacuum overnight to yield the polymer-supported P(Br)-2, 4-(MeO)$_2$—C$_6$H$_3$. $^{31}$P NMR (122 MHz, CDCl$_3$): δ153.8 ppm.

A suspension of this polymer-bound compound (2.0 g, 1.82 mmol, 0.908 mm/g) and I-PrMgBr (12.0 mmol, 1.0 M in THF solution) in 10 mL of THF was refluxed overnight before the solution was filtered off. The resulting resin was washed with THF (3×20 mL), CH$_2$Cl$_2$ (3×10 mL), Me$_2$CHOH (2×10 mL), THF/H$_2$O (70/30 volume ratio, 2×20 mL) and hexane (3×10 mL). The resin was dried in vacuum overnight. 31P NMR (122 MHz, CDCl$_3$): δ60.7 ppm.

A suspension of polymer-bound P(i-Pr)-2, 4-(MeO)$_2$—C$_6$H$_3$ (2.0 g, 1.876 mmol, 0.938 mm/g) and H$_2$O (0.5 g, 28 mm) in 10 mL of THF was refluxed overnight before the resin was filtered off and washed with hexane (3×10 mL). Removal of solvents and excess H$_2$O from the filtrates by vacuum afforded 100 mg (23% yield) of P(i-Pr)-2, 4-(MeO)$_2$—C$_6$H$_3$. It was >95% pure by $^1$H NMR and GC/MS. $^{31}$P NMR (202 MHz, CDCl$_3$): δ35.8 (s) ppm. $^{31}$P NMR ($^1$H-coupled, 202 MHz, CDCl$_3$): δ35.8 (d, H$_{P-H}$=485.8 Hz) ppm. $^1$H NMR (500 MHz, CDCl$_3$): δ7.57 (m, 1H), 7.25 (d, H$_{P-H}$=485.2 Hz, 1H), 6.48 (m, 1H), 6.37 (m, 1H), 3.76 (d, J=15.2 Hz, 3H), 3.70 (d, J=38.7 Hz, 3H), 2.18 (m, 1H), 1.12–0.81 (m, 6H). $^{13}$C NMR (125 MHz, CDCl$_3$): 165.0, 161.8, 135.1, 105.6, 105.5, 98.2, 67.9, 55.6, 27.4, 14.5 ppm. MS: 229.2 (M+1).

Experiment 4

Synthesis of (Me$_3$C)$_2$PH(S)

A mixture of (Me$_3$C)$_2$PH (5.0 g, 34.2 mm), and S$_8$ (1.096 g, 34.19 mm) in 150.0 mL of 1,4-dioxane was refluxed for 24 h. The resulting mixture was cooled to room temperature and filtered. Removal of solvent followed by sublimation (10$^{-3}$ torr/140) afforded 6.0 g (98% yield) of (Me$_3$C)$_2$PH(S). It was >95% pure by $^1$H NMR and GC/MS. $^{31}$P NMR (121 MHz, CDCl$_3$, $^1$H-decoupled): δ75.8 ppm. $^{31}$P NMR (121 MHz, CDCl$_3$, $^1$H-coupled): δ76.6 (d, J$_{p-H}$=417.1 Hz). $^1$H NMR (500 MHz, CDCl$_3$): δ5.84 (d, H$_{p-H}$=417.3 Hz, 1H), 1.33 (d, J$_{p-H}$=16.5 Hz, 18H). $^{13}$C NMR (125 MHz, CDCl$_3$): δ35.8 (d, J$_{P-C}$=42.2 Hz), 27.3 (d, J$_{P-C}$=2.46 Hz) ppm. IR (KBr): 2999, 2975, 2952, 2923, 2901, 2864, 2313, 1635, 1470, 1390, 1367, 1360, 1188, 1028, 1014, 903 cm$^{-1}$. HRMS: Calcd for C$_8$H$_{19}$PS: 179.1023. Found: 179.1018. Anal. Calcd for C$_8$H$_{19}$PS: C, 53.90; H, 10.74; P, 17.37. Found: C, 53.63; H, 10.60; P, 17.46.

Experiment 5

Synthesis of Ph$_2$PH(S)

A mixture of Ph$_2$PH (10.0 g, 53.7 mm), and S$_8$ (1.70 g, 53.0 mm) in 150.0 mL of 1,4-dioxane was refluxed for 24 h. The resulting mixture was cooled to room temperature and filtered. Removal of solvent followed by sublimation (10$^{-3}$ torr/150° C.) afforded Ph$_2$PH(S). It was >95% pure by $^1$H NMR and GC/MS. $^{31}$P NMR (121 MHz, CDCl$_3$, $^1$H-decoupled): δ23.8 ppm.

Experiment 6

Preparation of Pd-(t-Bu)$_2$P—SH Complex

Method A

A solution of 32.0 mg (0.112 mm) of Pd(COD)Cl$_2$ and 20.0 mg (0.112 mm) of (t-Bu)$_2$PH(S) in 2.0 mL of THF was boiled under reflux for 12 h. Examination of the reaction mixture by $^1$H-coupled $^{31}$P NMR at this point revealed only a singlet at δ145.2 ppm. After filtration, the removal of solvent under vacuum affords a brown solid. $^{31}$P NMR (121 MHz, CDCl$_3$, $^1$H-decoupled): δ146.3 ppm. $^{31}$P NMR (121 MHz, CDCl$_3$, $^1$H-coupled): δ145.2 (s). $^1$H NMR (500 MHz, CDCl$_3$): δ1.40 (d, J$_{P-H}$=18.4 Hz, 18H) ppm. $^{13}$C NMR (125 MHz, CDCl$_3$): δ45.2 (d, J$_{P-C}$=40.0 Hz), 27.5 ppm.

Method B

A solution of 50.0 mg (0.0546 mm) of Pd$_2$(dba)$_3$ and 20.0 mg (0.112 mm) of (t-Bu)$_2$PH(S) in 4.0 mL of 1,4-dioxane was boiled under reflux for 12 h. Examination of the reaction mixture by $^1$H-coupled $^{31}$P NMR at this point revealed a singlet at δ149.2 ppm as a major component.

Experiment 7

Preparation of [Bis-(di-t-butylphosphinous acid)] palladium chloride dimer {[(t-Bu)$_2$P(OH)]$_2$PdCl]}$_2$ Method A In the dry box, a solution of 1.608 g (8.90 mmol) of (Me$_3$C)$_2$P—Cl in 50 mL of 1,4-dioxane and 160.0 mg (8.90 mmol) of H$_2$O was stirred at room temperature for 10 min, and 1.0 g (4.45 mmol) of Pd(OAc)$_2$ was gradually added within 5 min. The resulting mixture was then removed from the dry box and refluxed for 5 h. The phosphorus-31 NMR spectrum of the reaction mixture at this point showed the δ125.5 (~5%), 123.5 (~45%), 123.3 (~45%) resonances, and no unchanged (Me$_3$C)$_2$PCl and (Me$_3$C)$_2$P(O)H. After cooling to room temperature the mixture was concentrated by rotary evaporation to afford 1.85 g (89% yield) of [Bis-(di-t-butylphosphinous acid)]palladium (I) chloride dimer. $^1$H NMR (300 MHz, CDCl$_3$): δ1.37 (d, J=14.57 Hz) ppm. $^{13}$C NMR (76 MHz, CDCl$_3$): δ41.9 (t, J=14.41 Hz), 29.48 (s) ppm. $^{31}$P NMR (121 MHz, CDCl$_3$): δ124.0 ppm.

$^1$H-coupled $^{31}$P NMR (121 MHz, CDCl$_3$): δ124.9 (s) ppm. Anal. Calcd for C$_{32}$H$_{76}$O$_4$P$_4$Pd$_2$: C, 41.21; H, 8.21; P, 13.28; Cl, 7.60. Found: C, 41.21; H, 8.66; P, 13.28; Cl, 7.54. The crystallographic sample was obtained by slow recrystallization from a mixture of dichloromethane and hexane.

Method B

A 500 mL of round-bottomed flask equipped with magnetic stir bar was charged with 1.469 g (8.90 mm) of (Me$_3$C)$_2$PH(O) which was generated from (Me$_3$C)$_2$PCl and H$_2$O in CH$_2$Cl$_2$, 1.0 g (4.45 mm) of Pd(OAc)$_2$ and 100 mL of 1,4-dioxane. The resulting mixture was then heated to a gentle reflux under open-to-air condition for 20 h. The phosphorus-31 NMR spectrum of the reaction mixture showed the δ125.5 (~5%) and 123.4 (~95%) resonance, and no unchanged (Me$_3$C)$_2$PH(O). After cooling to room temperature the solution was concentrated by rotary evaporation, the residue was extracted with hexane (10×100 mL). The extracts were combined, dried under vacuum to afford 1.80 g (87% yield) of yellow solids. It was >95% pure by $^1$H and $^{31}$P NMR. $^{31}$P NMR (121 MHz, CDCl$_3$): δ124.0 ppm.

Method C

A 500 mL of round-bottomed flask equipped with magnetic stir bar was charged with 1.160 g (7.15 mmol) of (Me$_3$C)$_2$PH(O), 0.621 g (3.50 mmol) of PdCl$_2$ and 100 mL of THF. The resulting mixture was then heated to a gentle reflux under open-to-air condition for 14 h. The phosphorus-31 NMR spectrum of the reaction mixture showed the δ123.5 (~5%), 122.7 (~95%) resonances, and no unchanged (Me$_3$C)$_2$PH(O). After cooling to room temperature the solution was concentrated by rotary evaporation to afford 1.80 g (87% yield) of (di-t-butylphosphinous acid)palladium (I) chloride dimer.

Method D

In the dry box, a solution of 4.076 g (22.56 mmol) of (Me$_3$C)$_2$P—Cl in 135 mL of THF and 407 mg (22.61 mmol) of H$_2$O was stirred at room temperature for 10 min, and 2.0 g (11.28 mmol) of PdCl$_2$ was gradually added within 5 min. The resulting mixture was then removed from the dry box and refluxed for 24 h. The phosphorus-31 NMR spectrum of the reaction mixture at this point showed the δ123.5 (~5%), 122.7 (~80%) as major resonances. After cooling to room temperature the mixture was concentrated by rotary evaporation to afford 4.30 g (82% yield) of (di-t-butylphosphinous acid)palladium (I) chloride dimer.

X-RAY CRYSTAL STRUCTURE ANALYSIS

Crystal Data

C$_{32}$H$_{76}$Cl$_2$O$_4$P$_4$Pd$_2$, from dichloromethane/hexane, light gold, square prism, ~0.20×0.04×0.04 mm, orthorhombic, P2$_1$2$_1$2$_1$, a=14.7052(13) Å, b=15.3071(13) Å, c=19.0752(17) Å, alpha=90°, beta=90°, gamma=90°, Vol=4293.7(7) Å3, Z=4, T=−100.° C. Formula weight=930.49, Density=1.439mg/m$^3$, μ(Mo)=1.14 mm−1

Data Collection

Bruker SMART 1K CCD system, MoKalpha radiation, standard focus tube, anode power=50 kV×40 mA, crystal to plate distance=4.9 mm, 512×512 pixels/frame, multirun data aquisition, total scans=9, total frames=6170, oscillation/frame=−0.30°, exposure/frame=10.0 sec/frame, maximum detector swing angle=−42.0°, beam center=(254.93,252.33), in plane spot width=1.23, omega half width=0.54, SAINT integration, 1936, hkl min/max=(−19, 17, −20, 20, −25, 25), data collected=40411, unique data=10392, two-theta range=3.42 to 56.60°, completeness to two-theta 56.60=98.90%, R(int)=0.0677, SADABS correction applied.

Solution and Refinement

Structure solved using XS(Shelxtl), refined using shelxtl software package, refinement by full-matrix least squares on F 2, scattering factors from Int. Tab. Vol C Tables 4.2.6.8 and 6.1.1.4, number of data=10392, number of restraints=0, number of parameters=430, data/parameter ratio=24.17, goodness-of-fit on F2=0.80, R indices[I>4sigma(I)] R1=0.0372, wR2=0.0579, R indices(all data) R1=0.0779, wR2=0.0652, max difference peak and hole=1.398 and −0.430 e/Å3, refined flack parameter=0.00(12), All hydrogen atoms except H2A and H3A have been idealized as riding hydrogens. The rotation of the methyl groups are refined.

Results

The asymmetric unit contained one molecule with thermal ellipsoids drawn to the 50% probability level. The structure was a racemic twin and the flack parameter had been refined as a full matrix parameter to a value of 0.41(2). The OH group on each side of the molecule formed a symmetric hydrogen bond with the O—. The +2 charge of each palladium atom was balanced by the O-1 and CL-1 atoms.

Experiment 8

Preparation of (Di-t-butylphosphinous acid) palladium Dichloride Dimer [(t-Bu)$_2$P(OH) PdCl$_2$]$_2$ Method A A 500 mL of round-bottomed flask equipped with magnetic stir bar was charged with 1.160 g (7.15 mm) of (Me$_3$C)$_2$PH(O), 1.242 g (7.00 mm) of PdCl$_2$ and 100 mL of THF. The resulting mixture was then heated to a gentle reflux under open-to-air condition for 20 h. The phosphorus-31 NMR spectrum of the reaction mixture showed the δ146.96 (singlet, ca. 95%) and 123.0 (singlet, ca. 5%) resonances, and no unchanged (Me$_3$C)$_2$PH(O). After cooling to room temperature, the solution was filtered and concentrated by rotary evaporation to afford 2.0 g of dichloro(di-t-butylphosphinous acid)palladium (II) dimer. $^1$H NMR (500 MHz, CDCl$_3$): δ5.23 (m, 1H), 1.43 (d, J=16.3 Hz, 18H) ppm. $^{13}$C NMR (125 MHz, CDCl$_3$): δ42.2 (d, J$_{P-C}$=25.4 Hz), 28.0 ppm. $^{31}$P NMR (CDCl$_3$, 202 MHz): δ145.0 ppm. Anal. Calcd for C$_{16}$H$_{38}$P$_2$O$_2$C$_{14}$Pd$_2$: C, 28.3; H, 5.64. Found: C, 27.86; H, 5.47. The crystallographic sample was obtained by slow recrystallization from a mixture of dichloromethane and hexane.

X-RAY CRYSTAL STRUCTURE ANALYSIS

Crystal Data

C8 H19 C12 O P Pd, from dichloromethane/hexane, red/orange, irregular block, ~0.32×0.32×0.16 mm, triclinic, P-1, a=7.8076(10) Å, b=8.0145(10) Å, c=10.4598(10) Å, alpha=84.127(2)°, beta=84.870(2)°, gamma=87.923(2)°, Vol=648.23(13) Å3, Z=2, T=−100° C., Formula weight=339.50, Density=1.739mg/m3, μ(Mo)=1.93 mm−1

Data Collection

Bruker SMART 1K CCD system, MoKalpha radiation, standard focus tube, anode power=50 kV×40 mA, crystal to plate distance=4.9 mm, 512×512 pixels/frame, hemisphere data aquisition, total scans=4, total frames=1310, oscillation/frame=−0.30°, exposure/frame=8.0 sec/frame, maximum detector swing angle=−28.0°, beam center=(254.93,252.33), in plane spot width=1.74, omega half width=0.48, SAINT integration, 340, hkl min/max=(−10, 5, −10, 10, −13, 13), data collected=4226, unique data=2937, two-theta range=3.92 to 56.56°, completeness to two-theta 56.56=91.00%, R(int)=0.0131, SADABS correction applied.

Solution and Refinement

Structure solved using XS(Shelxtl), refined using shelxtl software package, refinement by full-matrix least squares on F 2, scattering factors from Int. Tab. Vol C Tables 4.2.6.8 and 6.1.1.4, number of data=2937, number of restraints=0, number of parameters=129, data/parameter ratio=22.77, goodness-of-fit on F2=1.07, R indices[I>4sigma(I)] R1=0.0243, wR2=0.0666, R indices(all data) R1=0.0265, wR2=0.0682, max difference peak and hole=0.539 and −0.941 e/Å3, All hydrogen atoms except H1 have been idealized as riding hydrogens. The rotation of the methyl groups are refined.

Results

The asymmetric unit contained one half of the molecule with thermal ellipsoids drawn to the 50% probability level.

Method B

A solution of 2.0 g (7.00 mmol) of Pd(COD)Cl$_2$ and 1.16 g (7.03 mmol) of (t-Bu)$_2$PH(O) in 100 mL of 1,4-dioxane was boiled under reflux for 17 h. Examination of the reaction mixture by $^1$H-coupled $^{31}$P NMR at this point revealed only a singlet at δ147.6 ppm. Solvent was removed from filtrate in vacuo and the residue was dissolved in CH$_2$Cl$_2$. Evaporation of the filtrate in vacuum followed by crystallization from a mixture of CH$_2$Cl$_2$/hexane (95:5 volume ratio) gave 2.0 g (84% yield) of dark brown [(t-Bu)$_2$P—(OH)PdCl$_2$]$_2$. $^1$H NMR (500 MHz, CDCl$_3$): δ5.23 (m, 1H), 1.43 (d, J=16.3 Hz, 18H) ppm. $^{13}$C NMR (125 MHz, CDCl$_3$): δ42.2 (d, J$_{P-C}$=25.4 Hz), 28.0 ppm. $^{31}$P NMR (CDCl$_3$, 202 MHz): δ145.0 ppm.

Method C

In the dry box, a solution of 1.019 g (5.64 mmol) of (Me$_3$C)$_2$P—Cl in 100 mL of THF and 102 mg (5.64 mmol) of H$_2$O was stirred at room temperature for 10 min, and 1.0 g (5.64 mmol) of PdCl$_2$ was gradually added within 5 min. The resulting mixture was then removed from the dry box and refluxed for 6 h. The phosphorus-31 NMR spectrum of the reaction mixture at this point showed the δ146.6 (singlet, ca. 70%) and 122.7 (singlet, ca. 30%) resonances. After the resulting mixture was refluxed for another 18 h, the crude product was shown by its phosphorus-31 NMR spectrum to be a mixture of the title complex 2 and di-t-butylphosphinechloride palladium chloride dimer with a phosphorus-31 NMR spectrum of δ164.7 (singlet) as major components in approximately equal amounts.

Experiment 9

Preparation of Di-t-butylphosphinechloride Palladium Chloride Dimer [(t-Bu)$_2$P(Cl)PdCl$_2$]$_2$ A solution of 3.0 g (10.5 mmol) of Pd(COD)Cl$_2$, 1.898 g (10.5 mmol) of (t-Bu)$_2$P—Cl and 200 mg (11.1 mmol) of H$_2$O in 100 mL of THF was boiled under reflux for 14 h. Examination of the reaction mixture by $^1$H-coupled $^{31}$P NMR at this point revealed only a singlet at δ164.7(singlet) ppm. After cooling to room temperature, the reaction mixture was filtered, and the residue was washed with CH$_2$Cl$_2$ (20 mL). Solvents were removed by rotary evaporation, and the resulting residue was washed with hexane (8×50 mL), dried in vacuo gave 3.2 g of dark brown [(t-Bu)$_2$P(Cl)Pd Cl$_2$]$_2$. The crystallographic sample was obtained by slow recrystallization from a mixture of dichloromethane and hexane.

X-RAY CRYSTAL STRUCTURE ANALYSIS

Crystal Data

C8 H18 Cl3 P Pd, from dichloromethane/hexane, red/orange, wedge, ~0.150×0.140×0.050 mm, orthorhombic, Pca21, a=14.8290(13) Å, b 11.9397(10) Å, c=14.7623(13) Å, Vol=2613.7(4) Å3, Z=8, T=−120.° C., Formula weight=357.94, Density 1.819mg/m3, μ(Mo)=2.11 mm-1.

Data Collection

Bruker SMART 1K CCD system, MoKalpha radiation, standard focus tube, anode power=50 kV×40 mA, crystal to plate distance=4.9 mm, 512×512 pixels/frame, hemisphere data aquisition , total scans=4, total frames=1330, oscillation/frame=−0.30°, exposure/frame=30.0 sec/frame, maximum detector swing angle=−28.0°, beam center=(254.93,252.33), in plane spot width=1.46, omega half width=0.81, SAINT integration, hkl min/max=(−19, 16, −15, 15, −19, 16), data input to shelx=16611, unique data=5405, two-theta range=3.42 to 56.58°, completeness to two-theta 56.58=98.20%, R(int-xl)=0.0216, SADABS correction applied.

Solution and Refinement

Structure solved using XS(Shelxtl), refined using shelxtl software package, refinement by full-matrix least squares on F 2, scattering factors from Int. Tab. Vol C Tables 4.2.6.8 and 6.1.1.4, number of data=5405, number of restraints=1, number of parameters=247, data/parameter ratio=21.88, goodness-of-fit on F2=1.06, R indices[I>4sigma(I)] R1=0.0174, wR2=0.0448, R indices(all data) R1=0.0181, wR2=0.0452, max difference peak and hole=0.768 and −0.427 e/Å3, refined flack parameter=−0.005(16), All hydrogen atoms have been idealized as riding hydrogens. The rotation of the methyl groups are refined.

Results

The asymmetric unit contains one molecule with thermal ellipsoids drawn to the 50% probability level.

Experiment 10

Preparation of [Bis-(di-phenylphosphinous acid)] Palladium Chloride Dimer

Method A

In the dry box, a solution of 1.964 g (8.90 mmol) of Ph$_2$P—Cl in 100 mL of 1,4-dioxane and 180.0 mg (10.0 mmol) of H$_2$O was stirred at room temperature for 10 min, and 1.0 g (4.45 mmol) of Pd(OAc)$_2$ was gradually added within 5 min. The resulting mixture was then removed from the dry box and refluxed for 20 h. The phosphorus-31 NMR spectrum of the reaction mixture at this point showed the δ78.1 (~70%), 30.2 [~30% Ph$_2$P(O)H]resonances.

Method B

In the dry box, a solution of 13.1 g (56.4 mmol) of Ph$_2$P—Cl in 100 mL of THF and 1.2 g (66.7 mmol) of H$_2$O was stirred at room temperature for 10 min, and 5.0 g (28.2 mmol) of PdCl$_2$ was gradually added within 5 min. The resulting mixture was then removed from the dry box and refluxed for 15 h. The phosphorus-31 NMR spectrum of the reaction mixture at this point showed the δ78.6 (~30%), 29.1 [~70% Ph$_2$P(O)H] resonances.

Experiment 11

Preparation of Di-isopropylphosphine Oxide (Me$_2$CH)$_2$PH(O)

Method A

In a dry box, a solution of 0.35 g (2.29 mmol) of (Me$_2$CH)$_2$P—Cl in 10 mL of CH$_2$Cl$_2$ was treated with 100 mg (5.5 mmol) of H$_2$O within 5 min. The resulting mixture was then removed from the dry box and refluxed for 10 min. The phosphorus-31 NMR spectrum of the reaction mixture at this point showed the δ65.7 resonance. The reaction mixture was dried under vacuum to afford 0.21 g (68% yield) of crude product.

Method B

A solution of 3.43 g (21.56 mmol) of (Me$_2$CH)$_2$P—Cl in 80 mL of hexane was treated with 835 mg (46.4 mmol) of H$_2$O within 5 min. The resulting mixture was stirred at room temperature for 24 h. The phosphorus-31 NMR spectrum of the reaction mixture at this point showed the δ65.7 resonance. The reaction mixture was dried under vacuum to afford 2.8 g (97% yield) of crude product.

Experiment 12

Preparation of Di-cyclohexylphosphine oxide Cy$_2$PH(O)

In a dry box, a solution of 0.42 g (1.80 mmol) of Cy$_2$P—Cl in 10 mL of CH$_2$Cl$_2$ was treated with 100 mg (5.5 mmol) of H$_2$O within 5 min. The resulting mixture was then removed from the dry box and refluxed for 10 min. The phosphorus-31 NMR spectrum of the reaction mixture at this point showed the δ59.7 resonance. The reaction mixture was dried under vacuum to afford 0.30 g (78% yield) of crude product.

Experiment 13

Preparation of (di-isopropylphosphinous acid) palladium dichloride dimer [(Me$_2$CH)$_2$P(OH)]PdCl$_2$]$_2$ In a dry box, a solution of 1.0 g (6.29 mmol) of (Me$_2$CH)$_2$P—Cl in 35 mL of THF and 0.4 g (22.2 mmol) of H$_2$O was stirred at room temperature for 10 min, and 1.115 g (6.29 mmol) of PdCl$_2$ was gradually added within 5 min. The resulting mixture was then removed from the dry box and refluxed for 15 h. The phosphorus-31 NMR spectrum of the reaction mixture at this point showed the δ138.2 (~70%), 117.8 {~20%, [(Me$_2$CH)$_2$P(OH)]$_2$PdCl$_2$]$_2$} and 63.5 [~10%, (Me$_2$CH)$_2$PH(O)] resonances. After solvents were removed by rotary evaporation, the residue was washed with hexane (10×15 mL), dried under vacuum to afford 1.4 g (72% yield) of yellowish solids with $^{31}$P NMR: δ142.5 ppm.

Experiment 14

Preparation of (di-cyclohexylphosphinous acid) palladium Dichloride Dimer [(Cy)$_2$P(OH)]PdCl$_2$]$_2$ In a dry box, a solution of 1.0 g (4.297 mmol) of Cy$_2$P—Cl in 10 mL of THF and 0.4 g (22.2 mmol) of H$_2$O was stirred at room temperature for 10 min, and 762 mg (4.297 mmol) of PdCl$_2$ was gradually added within 5 min. The resulting mixture was then removed from the dry box and refluxed for 16 h. The phosphorus-31 NMR spectrum of the reaction mixture at this point showed the δ133.1 resonance. After solvents were removed by rotary evaporation, the residue was washed with hexane (8×20 mL), dried under vacuum to afford 1.45 g (86% yield) of crude [(Cy)$_2$P(OH)]PdCl$_2$]$_2$.

Experiment 15

Synthesis of Di-tert-Butylphenylphosphine Oxide

A 50 mL of reactor equipped with magnetic stir bar was charged with 186 mg (0.20 mmol) of {[(t-Bu)$_2$P(OH)]$_2$PdCl}$_2$, 1.57 g (10.0 mmol) of bromobenzene, 1.62 g (10.0 mmol) of di-tert-butylphosphine oxide and 1.38 g (10.0 mmol) of K$_2$CO$_3$ in 20.0 mL of 1,4-dioxane. The resulting mixture was refluxed for 23 h to afford di-tert-butylphenylphosphine oxide. $^{31}$P NMR (CDCl$_3$, 121 MHz): δ51.9 ppm.

Experiment 16

Synthesis of Tri-phenylphosphine Oxide

A 20 mL of reactor equipped with magnetic stir bar was charged with 93 mg (0.10 mmol) of {[(t-Bu)$_2$P(OH)]$_2$PdCl}$_2$, 0.314 g (2.0 mmol) of bromobenzene, 0.404 g (2.0 mmol) of di-phenylphosphine oxide and 0.276 g (2.0 mmol) of K$_2$CO$_3$ in 5.0 mL of 1,4-dioxane. The resulting mixture was refluxed for 8 h to afford tri-phenylphosphine oxide. $^{31}$P NMR (CDCl$_3$, 121 MHz): δ30.3 ppm.

Experiment 17

Chiral Phosphine Oxide Ligands

Synthesis of Cy$_2$N—PCl$_2$: A mixture of 34.4 g (0.25 moles) of PCl$_3$ in 400 mL of hexane was treated with Cy$_2$NH (90.7 g, 0.50 moles) dropwise at ° C. for 30 min. The resulting white slurry was warmed to room temperature and stirred for 1 h, refluxed overnight before removal of Cy$_2$NH—HCl by filtration. The white solids were washed with hexane (2×100 mL). The combined filtrates were concentrated to give the crude Cy$_2$N—PCl$_2$ (54.0 g, 77% yield). $^{31}$P NMR (121 MHz, CD$_2$Cl$_2$): δ171.3 (s) ppm.

Synthesis of (R, R) Cy$_2$N—P(2, 5-Me$_2$C$_4$H$_6$): A solution of 2.0 g (7.09 mm) of Cy$_2$N—PCl$_2$ in 150 mL of THF was treated dropwise with LiAlH$_4$ (7.1 mL of a 1.0 M solution in Et$_2$O) at room temperature for 10 min and then the resulting reaction mixture was stirred at room temperature for an additional 2 h. The reaction process was monitored by $^{31}$P NMR which indicated only a singlet at δ−69.2 ppm. The THF solvent was removed under vacuum, and the residue was extracted with 3×50 mL of hexane. After addition of 100 mL of THF to the extracts, 5.6 mmol (3.5 mL of 1.6 M solution in hexane) of n-BuLi was added to the solution above dropwise. The resulting mixture was stirred at room temperature for 2 h before 1.0 g (5.55 mmol ) of (2S, 5S)-2,5-hexanediol cyclic sulfate in 10 mL of THF was added to the mixture dropwise. After the solution was stirred for 1.5 h, n-BuLi (3.8 mL of a 1.6 M hexane solution, 1.1 eq) was again added dropwise via syringe. The resulting reaction mixture was allowed to stir overnight at room temperature before 3.0 mL of MeOH was added to quench excess n-BuLi remaining. After removal of solvent, the solid residue was extracted with hexane (4×60 mL), Concentration of the filtrate affords a crude product. MS: 312.2 [M(O)$^+$+H].

Synthesis of (R, R)(2, 5-Me$_2$C$_4$H$_6$)PH(O): A solution of 1.0 g (3.39 mmol) of of (R, R) Cy$_2$N—P(2, 5—Me$_2$C$_4$H$_6$) and 10 mL of HCl-ether solution (1.0 M in Et$_2$O) was stirred at room temperature for 2 h to afford a crude title compound.

Synthesis of (R, R)(2, 5—(Me$_2$CH)$_2$C$_4$H$_6$)PH(O): A suspension of polymer-bound N(t-Bu)PCl$_2$ (~20 g, ~17.8 mmol) and LiAlH$_4$ (100 mL, 100 mmol, 1.0 M solution in Et$_2$O) in 200 mL of THF was stirred at room temperature for 2 h before the solvents and excess reagent were filtered off. The resulting resin was washed with THF (3×100 mL) and hexane (3×100 mL) before n-BuLi (64 mmol, 1.6 M solution in hexane) was added. The suspension was stirred at room temperature over 3 h before the excess reagent and solvent were filtered off. The resulting resin was washed with THF (3×50 mL) and hexane (2×100 mL). The resin above and 3.1 g of (2S, 5S)-2,5-(i-Pr)$_2$C$_4$H$_6$SO$_4$ (cyclic sulfate) in 300 mL of THF were stirred at room temperature overnight before n-BuLi (20.0 mmol, 1.6 M solution in hexane) was added. The mixture was stirred at room temperature for 4 h, and the solvents and excess reagents were filtered off. The resulting resin was washed with THF (2×150 mL), hexane (2×150 mL) and CH$_2$Cl$_2$ (2×100 mL). The resin above and HCl-ether solution were stirred at room temperature to afford a crude title compound.

EXAMPLES

A. Reactions of Amines with Aryl Halides

Example 1

Synthesis of 1-phenylpiperidine

Method A

In a drybox, 14.4 mg (0.087 mmol) of (Me$_3$C)$_2$PH(O) from Experiment 2, 20.0 mg (0.0218 mmol) of Pd$_2$(dba)$_3$ (dba=bis(dibenzylideneacetone)) and 4.0 mL of toluene were loaded into a reactor (20 mL) equipped with a magnetic stir bar. The resulting mixture was stirred at room temperature overnight. Next, 144 mg (1.5 mmol) of NaOtBu was added into the mixture above, followed by syringing 122 μl (1.2 mmol) of PhCl, and 100 μl (1.0 mmol) of piperidine into the reactor. The resulting mixture was refluxed for 5 h. The reaction mixture was then cooled to room temperature, chromatographed on silicon gel using ethyl acetate/hexane (5% volume ratio) as eluant. The eluate was concentrated by rotary evaporation followed by high vacuum to yield 82 mg (51% yield) of N-phenylpiperidine. It was >95% pure by $^1$H NMR and GC/MS. $^1$H NMR (500 MHz, CDCl$_3$): δ7.15 (m, 2H), 6.84 (m, 2H), 6.72 (m, 1H), 3.06 (t, J=5.48 Hz, 4H), 1.61 (m, 4H), 1.48 (m, 2H) ppm. $^{13}$C NMR (125 MHz, CDCl$_3$): d 152.3, 129.0, 119.2, 116.5, 50.7, 25.9, 24.4 3 ppm. MS: Calculated for C$_{11}$H$_{15}$N(M$^+$): 161.3. Found: 162.3 (M$^+$+H).

Method B

A 50 mL of reactor equipped with magnetic stir bar was charged with 340 mg (0.50 mmol) of {[(t-Bu)$_2$P(OH)]PdCl$_2$}$_2$ (from Experiment 8), 1.12 g (10.0 mmol) of chlorobenzene, 1.02 g (12.0 mmol) of piperidine and 1.35 g (14.0 mmol) of NaO(t-Bu) in 20.0 mL of toluene. The resulting mixture was refluxed for 16 h before the reaction was cooled to room temperature and quenched with 50 mL of H$_2$O. The mixture was transferred to a separatory funnel, and diluted with 300 mL of diethyl ether. The layers were separated, and organic layer was washed with H$_2$O (2×30 mL), brine (30 mL), and dried over mgSO$_4$, filtered, and the ether removed from the filtrate by rotary evaporation. The resulting residue was chromatographed on silicon gel with hexane/ethyl acetate (50:1 volume ratio). The eluate was concentrated by rotary evaporation followed by high vacuum to give 700 mg (43% yield) of 1-phenylpiperidine.

Method C

A 50 mL of reactor equipped with magnetic stir bar was charged with 35 mg (0.05 mmol) of {[(t-Bu)$_2$P(OH)]PdCl$_2$}$_2$ (from Experiment 8), 1.57 g (10.0 mmol) of bromobenzene, 1.02 g (12.0 mmol) of piperidine and 1.35 g (14.0 mmol) of NaO(t-Bu) in 20.0 mL of toluene. The resulting mixture was refluxed for 5 h before the reaction was cooled to room temperature and quenched with 50 mL of H$_2$O. The mixture was transferred to a separatory funnel, and diluted with 300 mL of diethyl ether. The layers were separated, and organic layer was washed with H$_2$O (2×30 mL), brine (30 mL), and dried over mgSO$_4$, filtered, and the ether removed from the filtrate by rotary evaporation. The resulting residue was chromatographed on silicon gel with hexane/ethyl acetate (50:1 volume ratio). The eluate was concentrated by rotary evaporation followed by high vacuum to give 670 mg (42% yield) of 1-phenylpiperidine.

Method D

In the drybox, 20.0 mg (0.087 mmol) of (Me$_2$CH)PH(O) (2,4—(MeO)$_2$C$_6$H$_3$) from Experiment 3, 20.0 mg (0.0218 mmol) of Pd$_2$(dba)$_3$ and 3.0 mL of dioxane were loaded into a reactor (20 mL) equipped with a magnetic stir bar. The resulting mixture was stirred at room temperature for 10 min. Next, 144 mg (1.5 mmol) of NaOtBu was added into the mixture above, followed by syringing 122 μl (1.2 mmol) of PhCl, and 100 μl (1.0 mmol) of piperidine into the reactor. The resulting mixture was refluxed for 8 h. The reaction mixture was then cooled to room temperature, chromatographed on silicon gel using ethyl acetate/hexane (5% volume ratio) as eluant. The eluate was concentrated by rotary evaporation followed by high vacuum to yield 59 mg (37% yield) of 1-phenylpiperidine. It was >95% pure by $^1$H NMR and GC/MS. $^1$H NMR (500 MHz, CDCl$_3$): δ7.15 (m, 2H), 6.84 (m, 2H), 6.72 (m, 1H), 3.06 (t, J=5.48 Hz, 4H), 1.61 (m, 4H), 1.48 (m, 2H) ppm. $^{13}$C NMR (125 MHz, CDCl$_3$): δ152.3, 129.0, 119.2, 116.5, 50.7, 25.9, 24.4 3 ppm. MS: Calcd for C$_{11}$H$_{15}$N(M$^+$): 161.3. Found: 162.3 (M$^+$+H).

Example 2

The general procedure from Example 1A was followed using 4-chloro-benzotrifluoride (650 mg, 3.6 mmol) and piperidine (258 mg, 3.0 mmol) with Pd$_2$(dba)$_3$ (55 mg, 0.081 mmol) and (Me$_3$C)$_2$PH(O) (21.0 mg, 0.126 mmol) and NaOtBu (432 mg, 4.5 mmol) in 6.0 mL of toluene. After 48 h, the reaction mixture was chromatographed with 5% ethyl acetate/hexane to give 161 mg (23% yield) of 4-piperidinobenzotrifluoride. It was >95% pure by $^1$H NMR and GC/MS. $^1$H NMR (500 MHz, CDCl$_3$): δ7.36 (d, J=8.78 Hz, 2H), 6.82 (d, J=8.79 Hz, 2H), 3.18 (m, 4H), 1.60 (m, 4H), 1.54 (m, 2H) ppm. $^{13}$C NMR (125 MHz, CDCl$_3$): d 153.7, 127.6, 126.3, 114.5, 49.2, 25.4, 24.2 ppm. MS: Calculated for C$_{12}$H$_{14}$F$_3$N(M$^+$): 229.1. Found: 230.2 (M$^+$+H).

Example 3

The general procedure from Example 1A was followed using chlorobenzene (135 mg, 1.2 mmol) and aniline (93 mg, 1.0 mmol) with Pd$_2$(dba)$_3$ (25 mg, 0.027 mmol) and (Me$_3$C)$_2$PH(O) (7.0 mg, 0.042 mmol) and NaOtBu (144 mg, 1.5 mmol) in 2.0 mL of toluene. After 24 h, the reaction mixture was chromatographed with 5% ethyl acetate/hexane to give 51 mg (30% yield) of diphenylamine. It was >95% pure by $^1$H NMR and GC/MS. $^1$H NMR (500 MHz, CDCl$_3$): δ7.18 (m, 4H), 6.99 (d, J=7.68 Hz, 4H), 6.84 (t, J=7.34 Hz, 2H), 5.59 (br, 1H) ppm. $^{13}$C NMR (125 MHz, CDCl$_3$): d 143.1, 129.3, 120.9, 117.8 ppm. MS: Calculated for C$_{12}$H$_{11}$N(M$^+$): 169.1. Found: 170.3 (M$^+$+H).

Example 4

The general procedure from Example 1A was followed using 4-methyl-chlorobenzene (152 mg, 1.2 mmol) and piperidine (100 μl, 1.0 mmol) with Pd$_2$(dba)$_3$ (20 mg, 0.0218 mmol) and (Me$_3$C)$_2$PH(O) (14.5 mg, 0.0878 mmol) and NaOtBu (144 mg, 1.5 mmol) in 3.0 mL of toluene. After 12 h, the reaction mixture was chromatographed with 5% ethyl acetate/hexane to give 106 mg (81% yield) of N-(4-methylphenyl)piperidine. It was >95% pure by $^1$H NMR and GC/MS. $^1$H NMR (500 MHz, CDCl$_3$): δ6.92 (d, J=8.4 Hz, 2H), 6.72 (d, J=8.5 Hz, 2H), 2.95 (t, J=5.5 Hz, 4H), 2.13 (s, 3H), 1.58 (m, 4H),1.43 (m, 2H) ppm. $^{13}$C NMR (125 MHz, CDCl$_3$): δ150.3, 129.5, 128.6, 116.9, 51.2, 25.9, 24.3, 20.3 ppm. MS: Calculated for C$_{12}$H$_{17}$N(M$^+$): 175.1. Found: 176.1 (M$^+$+H).

Example 5

The general procedure from Example 1A was followed using PhCl (122 μl, 1.2 mmol) and p-toluidine (108 mg, 1.0 mmol) with Pd$_2$(dba)$_3$ (20 mg, 0.0218 mmol) and (Me$_3$C)$_2$PH(O) (14.5 mg, 0.0878 mmol) and NaOtBu (144 mg, 1.5 mmol) in 3.0 mL of toluene. After 12 h, the reaction mixture was chromatographed with 5% ethyl acetate/hexane to give 80 mg (44% yield) of N-phenyl-p-toluidine. It was >95% pure by $^1$H NMR and GC/MS. $^1$H NMR (500 MHz, CDCl$_3$): δ7.13 (t, J=7.91 Hz, 2H), 6.98 (m, 2H), 6.89 (m, 4H), 6.78 (t, J=7.32 Hz, 1H), 5.46 (s, br. 1H), 2.20 (s, 3H) ppm. $^{13}$C NMR (125 MHz, CDCl$_3$): d 143.9, 140.3, 130.8, 129.8, 129.2, 120.2, 118.9, 116.8, 20.6 ppm. MS: Calculated for C$_{13}$H$_{13}$N(M$^+$): 183.3. Found: 184.1 (M$^+$+H).

Example 6

The general procedure from Example 1A was followed using 4-chloroanisole (171 mg, 1.2 mmol) and piperidine (100 μl, 1.0 mmol) with Pd$_2$(dba)$_3$ (20 mg, 0.0218 mmol)

and (Me₃C)₂PH(O) (14.5 mg, 0.0878 mmol) and NaOtBu (144 mg, 1.5 mmol) in 4.0 mL of toluene. After 12 h, the reaction mixture was chromatographed with 5% ethyl acetate/hexane to give 128 mg (67% yield) of N-(4-methoxyphenyl)piperidine. It was >95% pure by $^1$H NMR and GC/MS. $^1$H NMR (500 MHz, CDCl₃): δ6.81 (d, J=9.11 Hz, 2H), 6.72 (d, J=9.11 Hz, 2H), 3.65 (s, 3H), 2.92 (t, J=5.46 Hz, 4H), 1.60 (m, 4H), 1.46 (m, ppm. $^{13}$C NMR (125 MHz, CDCl₃): δ153.5, 146.8, 118.6, 114.3, 55.4, 52.2, 26.1, 24.1 ppm.

Example 7

The general procedure from Example 1A was followed using chlorobenzene (135 mg, 1.2 mmol) and piperidine (86 mg, 1.0 mmol) with Pd₂(dba)₃ (20 mg, 0.0218 mmol) and (Me₂CH)PH(O)(Ph) from Experiment 1, (7.1 mg, 0.0424 mmol) and NaOtBu (144 mg, 1.5 mmol) in 2.0 mL of 1,2-dimethoxyethane. After 5 h, the reaction mixture was chromatographed with 5% ethyl acetate/hexane to give 17 mg (11% yield) of 4-phenylpiperidine. It was >95% pure by $^1$H NMR and GC/MS. $^1$H NMR (500 MHz, CDCl₃): δ7.15 (m, 2H), 6.84 (m, 2H), 6.72 (m, 1H), 3.06 (t, J=5.48 Hz, 4H), 1.61 (m, 4H), 1.48 (m, 2H) ppm. $^{13}$C NMR (125 MHz, CDCl₃): δ152.3, 129.0, 119.2, 116.5, 50.7, 25.9,24.4 3 ppm. MS: Calculated for C₁₁H₁₅N(M⁺): 161.3. Found: 162.3 (M⁺+H).

(OH)₂ (1.2 mmol) with Pd₂(dba)₃ (20 mg, 0.0218 mmol) and (Me₃C)₂PH(O) from Experiment 2 (14.5 mg, 0.0878 mmol) and CsCO₃ (651 mg, 2.0 mmol) in 4.0 mL of 1,4-dioxane. After 24 h, the reaction mixture was chromatographed with 5% ethyl acetate/hexane to give 127 mg (63% yield) of 4-phenyltoluene. It was >95% pure by $^1$H NMR and GC/MS. $^1$H NMR (500 MHz, CDCl₃): δ7.74 (d, J=7.50 Hz, 2H), 7.65 (d, J=8.05 Hz, 2H), 7.57 (m, 2H), 7.47 (m, 1H), 7.40 (m, 2H), 2.54 (s, 3H) ppm. $^{13}$C NMR (125 MHz, CDCl₃): δ141.1, 138.3, 136.9, 129.4, 128.6, 126.9, 126.8, 21.0 ppm.

Method B

The general procedure above was followed using 4-methylchlorobenzene (127 mg, 1.0 mmol) and PhB(OH)₂ (183 mg, 1.5 mmol) with Pd₂(dba)₃ (20 mg, 0.0218 mmol) and PhPH(O)(CHMe₂) from Experiment 1 (14.7 mg, 0.0874 mmol) and CsF (456 mg, 3.0 mmol) in 4.0 mL of 1,4-dioxane. After 12 h, the reaction mixture was chromatographed with 5% ethyl acetate/hexane to give 52 mg (31% yield) of 4-phenyltoluene. It was >95% pure by $^1$H NMR and GC/MS.

Example 10

In the drybox, 9.6 mg (0.058 mmol) of (Me₃C)₂PH(O) from Experiment 2, 13.3 mg (0.0145 mmol) of Pd₂(dba)₃ and 3.0 mL of 1,4-dioxane were loaded into a reactor (20

TABLE 1

| Example | Phosphine oxide | Aryl compound | Amine | Product | Yield |
| --- | --- | --- | --- | --- | --- |
| 1A | (Me₃C)₂PH(O) | chlorobenzene | piperidine | 1-phenylpiperidine | 51% |
| 1B | {[(t-Bu)₂P(OH)]₂PdCl}₂ | chlorobenzene | piperidine | 1-phenylpiperidine | 43% |
| 1C | {[(t-Bu)₂P(OH)]PdCl₂}₂ | chlorobenzene | piperidine | 1-phenylpiperidine | 42% |
| 1D | (Me₂CH)PH(O)(Ph) | chlorobenzene | piperidine | 1-phenylpiperidine | 11% |
| 2 | (Me₃C)₂PH(O) | 4-chlorobenzotriflouride | piperidine | 4-piperidinobenzotriflouride | 23% |
| 3 | (Me₃C)₂PH(O) | chlorobenzene | aniline | diphenylamine | 30% |
| 4 | (Me₃C)₂PH(O) | 4-methylchlorobenzene | piperidine | N-(4-methylphenyl)piperidine | 61% |
| 5 | (Me₃C)₂PH(O) | chlorobenzene | p-toluidine | N-phenyl-p-toluidine | 44% |
| 6 | (Me₃C)₂PH(O) | 4-chloroanisole | piperidine | N-(4-methylphenyl)piperidine | 67% |
| 7 | (Me₂CH)PH(O)(2,4-(MeO)₂C₆H₃) | chlorobenzene | piperidine | 1-phenylpiperidine | 37% |

B. Reactions of Arylboronic Acids with Aryl Halides

Example 8

In the drybox, 14.4 mg (0.087 mmol) of (Me₃C)₂PH(O) from Experiment 2, 20.0 mg (0.0218 mmol) of Pd₂(dba)₃ and 4.0 mL of 1,4-dioxane were loaded into a reactor (20 mL) equipped with a magnetic stir bar. The resulting mixture was stirred at room temperature overnight. Next, 651 mg (2.0 mmol) of CSCO₃ and 146.3 mg (1.2 mm) of PhB(OH)₂ were added into the mixture above, followed by syringing 122 μl (1.2 mmol) of PhCl into the reactor. The resulting mixture was refluxed for 24 h. The reaction mixture was then cooled to room temperature, chromatographed on silicon gel using ethyl acetate/hexane (5% volume ratio) as eluant. The eluate was concentrated by rotary evaporation followed by high vacuum to yield 163 mg (88% yield) of biphenyl. It was >95% pure by $^1$H NMR and GC/MS. $^1$H NMR (500 MHz, CDCl₃): δ7.77 (d, J=7.75 Hz, 4H), 7.60 (t, J=7.65 Hz, 4H), 7.50 (t, J=7.38 Hz, 2H).ppm. $^{13}$C NMR (125 MHz, CDCl₃): δ141.2, 128.7, 127.2, 127.1 ppm.

Example 9
Method A

The general procedure from Example 8 was followed using 4-methylchlorobenzene (152 mg, 1.2 mmol) and PhB mL) equipped with a magnetic stir bar. The resulting mixture was stirred at room temperature overnight. Next, 143.0 mg (1.0 mm) of 4-chloroanisole, 182.9 mg (1.5 mm) of PhB(OH)₂ and 456 mg (3.0 mmol) of CsF were added into the reactor. The resulting mixture was refluxed for 24 h. The reaction mixture was then cooled to room temperature, chromatographed on silicon gel using ethyl acetate/hexane (5% volume ratio) as eluant. The eluate was concentrated by rotary evaporation followed by high vacuum to yield 179 mg (97% yield) of 4-phenylanisole. It was >95% pure by $^1$H NMR and GC/MS. $^1$H NMR (500 MHz, CDCl₃): δ7.45 (m, 4H), 7.32 (m, 2H), 7.21 (m, 1H), 6.88 (d, J=8.72 Hz, 2H), 3.74 (s, 3H) ppm. $^{13}$C NMR (125 MHz, CDCl₃): δ159.2, 140.8, 133.8, 128.7, 128.1, 126.7, 126.6, 114.2, 55.3 ppm.

Example 11

The general procedure from Example 12 was followed using 2-chloro-anisole (143 mg, 1.0 mmol) and 4—MeC₆H₄B(OH)₂ (204 mg, 1.5 mmol) with Pd₂(dba)₃ (13.3 mg, 0.0145 mmol) and (Me₃C)₂PH(O) from Experiment 2 (9.6 mg, 0.058 mmol) and CsF (456 mg, 3.0 mmol) in 4.0 mL of 1,4-dioxane. After 24 h, the reaction mixture was chromatographed with 5% ethyl acetate/hexane to give 165 mg (83% yield) of 2-(4-methylphenyl)anisole. It was >95% pure by $^1$H NMR and GC/MS. $^1$H NMR (500 MHz, CDCl$_3$): δ7.32 (d, J=8.06 Hz, 2H), 7.18 (m, 2H), 7.10 (d, J=7.88 Hz, 2H), 6.92–6.84 (m, 2H), 3.67 (s, 3H), 2.28 (s, 3H) ppm. $^{13}$C NMR (125 MHz, CDCl$_3$): δ156.5, 136.5, 135.6, 130.7, 129.4, 128.7, 128.3, 120.8, 111.2, 55.5, 21.1 ppm.

Example 12

Method A

The general procedure from Example 12 was followed using 4-chloroanisole (143 mg, 1.0 mmol) and 4—MeOC$_6$H$_4$B(OH)$_2$ (228 mg, 1.5 mmol) with Pd$_2$(dba)$_3$ (13.3 mg, 0.0145 mmol) and (Me$_3$C)$_2$PH(O) from Experiment 2 (9.6 mg, 0.058 mmol) and CsF (456 mg, 3.0 mmol) in 3.0 mL of 1,4-dioxane. After 24 h, the reaction mixture was chromatographed with 5% ethyl acetate/hexane to give 213 mg (99% yield) of 4-(4-methoxyphenyl)anisole. It was >95% pure by $^1$H NMR and GC/MS. $^1$H NMR (500 MHz, CDCl$_3$): δ7.38 (d, J=8.68 Hz, 4H), 6.86 (d, J=8.68 Hz, 4H), 3.74 (s, 6H) ppm. $^{13}$C NMR (125 MHz, CDCl$_3$): δ158.7, 133.5, 127.7, 114.2, 55.3 ppm.

Method B

In the drybox, 20.0 mg (0.0876 mmol) of (Me$_2$CH)PH(O)(2,4—(MeO)$_2$C$_6$H$_3$) from Experiment 3, 20 mg (0.0218 mm) of Pd$_2$(dba)$_3$ and 5.0 mL of 1,4-dioxane were loaded into a reactor (20 mL) equipped with a magnetic stir bar. The resulting mixture was stirred at room temperature overnight. Next, 143.0 mg (1.0 mm) of 4-chloroanisole, 228 mg (1.5 mm) of 4—MeOC$_6$H$_4$B(OH)$_2$ and 456 mg (3.0 mmol) of CsF were added into the reactor. The resulting mixture was refluxed for 60 h. The reaction mixture was then cooled to room temperature, chromatographed on silicon gel using ethyl acetate/hexane (5% volume ratio) as eluant. The eluate was concentrated by rotary evaporation followed by high vacuum to yield 213 mg (99% yield) of p-(4-methoxyphenyl)anisole. It was >95% pure by $^1$H NMR and GC/MS. $^1$H NMR (500 MHz, CDCl$_3$): δ7.38 (d, J=8.68 Hz, 4H), 6.86 (d, J=8.68 Hz, 4H), 3.74 (s, 6H) ppm. $^{13}$C NMR (125 MHz, CDCl$_3$): δ158.7, 133.5, 127.7, 114.2, 55.3 ppm. Anal Calcd for C$_{14}$H$_{14}$O$_2$: C, 78.48; H, 6.59. Found: C, 78.44; H, 6.53.

reactor (100 mL). Next, 2-chloroanisole (1.43 g, 10.0 mm), C$_6$H$_5$B(OH)$_2$ (1.83 g, 15.0 mm) and CsF (4.56 mg, 30.0 mmol) were added into the mixture above. After the mixture was refluxed for 42 h, the reaction mixture was then cooled to room temperature, quenched with 50 mL of H$_2$O, and extracted with 300 mL of diethyl ether. The organic extracts were washed with H$_2$O (2×50 mL), brine (50 mL), and dried over mgSO$_4$, filtered, and the ether and dioxane removed from the filtrate by rotary evaporation. The resulting residue was chromatographed on silicon gel using hexane as eluant. The eluate was concentrated by rotary evaporation followed by high vacuum to give 1.81 g (98% yield) of 2-phenylanisole. It was >95% pure by $^1$H NMR and GC/MS. $^1$H NMR (500 MHz, CDCl$_3$): δ7.85 (d, J=7.05 Hz, 2H), 7.67 (m, 2H), 7.60 (m, 3H), 7.32 (m, 1H), 7.22 (m, 1H), 4.01 (s, 3H) ppm. $^{13}$C NMR (125 MHz, CDCl$_3$): δ156.4, 138.5, 130.7, 130.6, 129.4, 128.5, 127.8, 126.7, 120.7, 111.2, 55.3 ppm. HRMS Calcd for C$_{13}$H$_{12}$O: 185.0966. Found 185.0965. Anal. Calcd for C$_{13}$H$_{12}$O: C, 84.75; H, 6.57; O, 8.68. Found: C, 84.62; H, 6.65; O, 8.58.

Method B

A 50 mL of reactor equipped with magnetic stir bar was charged with 147.0 mg (0.89 mm) of (Me$_3$C)$_2$PH(O), 100 mg (0.445 mm) of Pd(OAc)$_2$ and 10 mL of 1,4-dioxane. The resulting mixture was then heated to a gentle reflux for 18 h. Next, 1.43 g (10.0 mm) of 2-chloroanisole, 1.83 g (15.0 mm) of PhB(OH)$_2$ and 4.56 g (30.0 mm) of CsF were added into the reactor. The resulting mixture was refluxed for 24 h.

The reaction mixture was then cooled to room temperature, quenched with 50 mL of H$_2$O, and extracted with 300 mL of diethyl ether. The organic extracts were washed with H$_2$O (2×50 mL), brine (50 mL), and dried over mgSO$_4$, filtered, and the ether and dioxane removed from the filtrate by rotary evaporation. The resulting residue was chromatographed on silicon gel using hexane as eluant. The eluate was concentrated by rotary evaporation followed by high vacuum to give 1.74 g (94% yield) of 2-phenylanisole. It was >95% pure by $^1$H NMR and GC/MS. $^1$H NMR (500 MHz, CDCl$_3$): δ7.85 (d, J=7.05 Hz, 2H), 7.67 (m, 2H), 7.60 (m, 3H), 7.32 (m, 1H), 7.22 (m, $^1$H), 4.01 (s, 3H) ppm. $^{13}$C

TABLE 2

| Example | Phosphine oxide | Aryl compound | Acid | Product | Yield |
| --- | --- | --- | --- | --- | --- |
| 8 | (Me$_3$C)$_2$PH(O) | chlorobenzene | PhB(OH)$_2$ | biphenyl | 88% |
| 9A | (Me$_3$C)$_2$PH(O) | 4-methylchlorobenzene | PhB(OH)$_2$ | 4-phenyltoluene | 63% |
| 9B | PhPH(O)(CHMe$_2$) | 4-methylchlorobenzene | PhB(OH)$_2$ | 4-phenyltoluene | 31% |
| 10 | (Me$_3$C)$_2$PH(O) | 4-chloroanisole | PhB(OH)$_2$ | 4-phenylanisole | 97% |
| 11 | (Me$_3$C)$_2$PH(O) | 2-chloroanisole | 4-MeC$_6$H$_4$B(OH)$_2$ | 2-(4-methylphenyl)-anisole | 83% |
| 12A | (Me$_3$C)$_2$PH(O) | 4-chloroanisole | 4-MeOC$_6$H$_4$B(OH)$_2$ | 4-(4-methoxyphenyl)-anisole | 99% |
| 12B | (Me$_2$CH)PH(O)(2,4-(MeO)$_2$C$_6$H$_3$) | 4-chloroanisole | 4-MeOC$_6$H$_4$B(OH)$_2$ | 4-(4-methoxyphenyl)-anisole | 99% |

Example 13

Synthesis of 2-phenylanisole

Method A

In the drybox, 110 mg (0.609 mmol) of (Me$_3$C)$_2$P—Cl, 67 mg (0.299 mmol) of Pd(OAc)$_2$ and 3.0 mL of CH$_2$Cl$_2$ were loaded into a reactor (10 mL) equipped with a magnetic stir bar. The resulting mixture was stirred at room temperature for 4 h before 60 mg (3.3 mmol) of H$_2$O was added. The mixture above was stirred at room temperature for 12 h. After removal of solvent and excess H$_2$O, the residue was dissolved in 15.0 mL of 1,4-dioxane, and transferred into a NMR (125 MHz, CDCl$_3$): δ156.4, 138.5, 130.7, 130.6, 129.4, 128.5, 127.8, 126.7, 120.7, 111.2, 55.3 ppm. HRMS Calcd for C$_{13}$H$_{12}$O: 185.0966. Found 185.0965. Anal. Calcd for C$_{13}$H$_{12}$O: C, 84.75; H, 6.57; O, 8.68. Found: C, 84.62; H, 6.65; O, 8.58.

Method C

A 100 mL of reactor equipped with magnetic stir bar was charged with 150 mg (0.161 mmol) of {[(t-Bu)$_2$P(OH)]$_2$PdCl}$_2$ (from Experiment 7), 1.43 g (10.0 mmol) of 2-chloroanisole, 1.83 g (15.0 mmol) of PhB(OH)$_2$ and 4.56 g (30.0 mmol) of CsF in 30.0 mL of dioxane. The resulting mixture was refluxed for 12 h until the starting material was completely consumed as judged by TLC. The reaction was cooled to room temperature, transferred to a separatory funnel, and diluted with 300 mL of diethyl ether. The layers were separated, and organic layer was washed with $H_2O$ (2×100 mL), brine (100 mL), and dried over $mgSO_4$, filtered, and the ether and dioxane removed from the filtrate by rotary evaporation. The resulting residue was chromatographed on silicon gel using 2% EtOAc/hexane as eluant. The eluate was concentrated by rotary evaporation followed by high vacuum to give 1.66 g (90% yield) of 2-phenylanisole.

Example 14

Synthesis of 3-phenylanisole

Method A

The procedure from Example above was followed using 110 mg (0.609 mmol) of $(Me_3C)_2P$—Cl, 67 mg (0.299 mmol) of $Pd(OAc)_2$, 60 mg (3.3 mmol) of $H_2O$, and 3-chloroanisole (1.43 g, 10.0 mm), $C_6H_5B(OH)_2$ (1.83 g, 15.0 mm) and CsF (4.56 mg, 30.0 mmol) in 15 mL of 1,4-dioxane. After the mixture was refluxed for 42 h, the reaction mixture was then cooled to room temperature, quenched with 50 mL of $H_2O$, and extracted with 300 mL of diethyl ether. The organic extracts were washed with $H_2O$ (2×50 mL), brine (50 mL), and dried over $mgSO_4$, filtered, and the ether and dioxane removed from the filtrate by rotary evaporation. The resulting residue was chromatographed on silicon gel using hexane as eluant. The eluate was concentrated by rotary evaporation followed by high vacuum to give 1.49 g (81% yield) of 3-phenylanisole. It was >95% pure by $^1H$ NMR and GC/MS.

Method B

A 100 mL of reactor equipped with magnetic stir bar was charged with 150 mg (0.161 mmol) of $\{[(t-Bu)_2P(OH)]_2 PdCl\}_2$ (from Experiment 7), 1.43 g (10.0 mmol) of 3-chloroanisole, 1.83 g (15.0 mmol) of $PhB(OH)_2$ and 4.56 g (30.0 mmol) of CsF in 30.0 mL of DME. The resulting mixture was refluxed for 12 h until the starting material was completely consumed as judged by TLC. The reaction was cooled to room temperature, transferred to a separatory funnel, and diluted with 300 mL of diethyl ether. The layers were separated, and organic layer was washed with $H_2O$ (2×100 mL), brine (100 mL), and dried over $mgSO_4$, filtered, and the ether and dioxane removed from the filtrate by rotary evaporation. The resulting residue was chromatographed on silicon gel using 2% EtOAc/hexane as eluant. The eluate was concentrated by rotary evaporation followed by high vacuum to give 1.73 g (94% yield) of 3-phenylanisole.

Example 15

Synthesis of 4-phenyltoluene

Method A

In the drybox, 1100 mg (6.09 mm) of $(Me_3C)_2P$—Cl, 670 mg (2.98 mmol) of $Pd(OAc)_2$ and 100 mL of 1,4-dioxane were loaded into a round-bottomed flask (250 mL) equipped with a magnetic stir bar. The resulting mixture was stirred at room temperature for 10 min before the flask was removed from the glove box. The mixture was refluxed under open-to-air condition. The progress of the reaction was monitored by phosphorus-31 NMR spectroscopy. After 2 h, approximately 95% of the reaction had proceeded. The phosphorus-31 NMR spectrum of the reaction mixture showed only the δ123.0 (singlet) resonance, and no unchanged $(Me_3C)_2P$—Cl. The reaction mixture was therefore cooled to room temperature and 600 mg (33.3 mmol) of $H_2O$ was added. The mixture above was refluxed for a further 15 min. Next, 12.659 g (100.0 mm) of 4-chlorotoluene, 13.41 g (110.0 mm) of $PhB(OH)_2$ and 22.785 g (150.0 mm) of CsF were added into the mixture above. The resulting mixture was refluxed for 18 h. The reaction mixture was then cooled to room temperature, quenched with 200 mL of $H_2O$, and extracted with diethyl ether (2×300 mL). The organic extracts were washed with $H_2O$ (2×250 mL), brine (250 mL), and dried over $mgSO_4$, filtered, and the ether and dioxane removed from the filtrate by rotary evaporation. The resulting residue was chromatographed on silicon gel using hexane as eluant. The eluate was concentrated by rotary evaporation followed by high vacuum to yield 4-phenyltoluene.

Method B

A 500 mL of round-bottomed flask equipped with magnetic stir bar was charged with 1.00 g (6.06 mm) of $(Me_3C)_2PH(O)$, 670 mg (2.98 mm) of $Pd(OAc)_2$ and 100 mL of 1,4-dioxane. The resulting mixture was then heated to a gentle reflux under open-to-air condition for 2 h. The phosphorus-31 NMR spectrum of the reaction mixture showed only the δ123.0 (singlet) resonance, and no unchanged $(Me_3C)_2PH(O)$. Next, 112.659 g (100.0 mm) of 4-chlorotoluene, 113.41 g (110.0 mm) of $PhB(OH)_2$ and 22.785 g (150 mm) of CsF were added into the flask. The resulting mixture was refluxed for 18 h. The reaction mixture was then cooled to room temperature, quenched with 200 mL of $H_2O$, and extracted with diethyl ether (2×300 mL). The organic extracts were washed with $H_2O$ (2×250 mL), brine (250 mL), and dried over $mgSO_4$, filtered, and the ether and dioxane removed from the filtrate by rotary evaporation. The resulting residue was chromatographed on silicon gel using hexane as eluant. The eluate was concentrated by rotary evaporation followed by high vacuum to yield 4-phenyltoluene.

Method C

A 100 mL of reactor equipped with magnetic stir bar was charged with 102 mg (0.15 mmol) of $\{[(t-Bu)_2P(OH)] PdCl_2\}_2$ (from Experiment 7), 1.13 g (10.0 mmol) of chlorobenzene, 2.04 g (15.0 mmol) of $MeC_6H_4B(OH)_2$ and 4.56 g (30.0 mmol) of CsF in 30.0 mL of 1,4-dioxane. The resulting mixture was refluxed for 15 h until the starting material was completely consumed as judged by TLC. The reaction was cooled to room temperature, transferred to a separatory funnel, and diluted with 300 mL of hexane. The layers were separated, and organic layer was washed with $H_2O$ (2×100 mL), brine (100 mL), and dried over $mgSO_4$, filtered, and the hexane and dioxane removed from the filtrate by rotary evaporation. The resulting residue was chromatographed on silicon gel using hexane as eluant. The eluate was concentrated by rotary evaporation followed by high vacuum to give 1.58 g (94% yield) of 4-phenyltoluene.

Example 16

Synthesis of 4-phenylanisole

A 100 mL of reactor equipped with magnetic stir bar was charged with 140 mg (0.15 mmol) of $\{[(t-Bu)_2P(OH)]_2 PdCl\}_2$ (from Experiment 7), 1.43 g (10.0 mmol) of 4-chloroanisole, 1.83 g (15.0 mmol) of $PhB(OH)_2$ and 4.56 g (30.0 mmol) of CsF in 30.0 mL of 1,4-dioxane. The resulting mixture was refluxed for 8 h until the starting material was completely consumed as judged by GC. The reaction was cooled to room temperature, transferred to a separatory funnel, and diluted with 300 mL of diethyl ether and 100 mL of $H_2O$. The layers were separated, and organic layer was washed with $H_2O$ (2×100 mL), brine (100 mL), and dried over mgSO$_4$, filtered, and the ether and dioxane removed from the filtrate by rotary evaporation. The resulting residue was chromatographed on silicon gel using 2% EtOAc/hexane as eluant. The eluate was concentrated by rotary evaporation followed by high vacuum to give 0.97 g (53% yield) of 4-phenylanisole.

Example 17

Synthesis of 4, 4'-dimethylbiphenyl

A 100 mL of reactor equipped with magnetic stir bar was charged with 102 mg (0.15 mmol) of {[(t-Bu)$_2$P(OH)]PdCl$_2$}$_2$ (from Experiment 7), 1.27 g (10.0 mmol) of 4-chlorotoluene, 2.04 g (15.0 mmol) of MeC$_6$H$_4$B(OH)$_2$ and 4.56 g (30.0 mmol) of CsF in 30.0 mL of 1,4-dioxane. The resulting mixture was refluxed for 20 h until the starting material was completely consumed as judged by TLC. The reaction was cooled to room temperature, transferred to a separatory funnel, and diluted with 300 mL of hexane. The layers were separated, and organic layer was washed with H$_2$O (2×100 mL), brine (100 mL), and dried over mgSO$_4$, filtered, and the hexane and dioxane removed from the filtrate by rotary evaporation. The resulting residue was chromatographed on silicon gel using hexane as eluant. The eluate was concentrated by rotary evaporation followed by high vacuum to give 1.2 g (66% yield) of the title compound.

Example 18

Synthesis of Biphenyl

Method A

A 100 mL of reactor equipped with magnetic stir bar was charged with 3.39 mg (0.00499 mmol) of {[(t-Bu)$_2$P(OH)]PdCl$_2$}$_2$ (from Experiment 7), 1.57 g (10.0 mmol) of bromobenzene, 1.46 g (12.0 mmol) of PhB(OH)$_2$ and 1.66 g (12.0 mmol) of K$_2$CO$_3$ in 7.0 mL of THF and 2.0 mL of H$_2$O. The resulting mixture was stirred at room temperature for 5 h. The reaction was transferred to a separatory funnel, and diluted with 300 mL of hexane and 50 mL of H$_2$O. The layers were separated, and organic layer was washed with H$_2$O (2×100 mL), brine (100 mL), and dried over mgSO$_4$, filtered, and the hexane and THF removed from the filtrate by rotary evaporation. The resulting residue was chromatographed on silicon gel using hexane as eluant. The eluate was concentrated by rotary evaporation followed by high vacuum to give 1.0 g (65% yield) of biphenyl.

Method B

A 100 mL of reactor equipped with magnetic stir bar was charged with 83.4 mg (0.303 mmol) of Ni(COD)$_2$, 50.0 mg (0.308 mmol) of (t-Bu)$_2$PH(O), 1.13 g (10.0 mmol) of Ph-Cl, 1.83 g (15.0 mmol) of PhB(OH)$_2$ and 4.56 g (30.0 mmol) of CsF in 15 mL of 1,4-dioxane. The resulting mixture was refluxed for 20 h. The reaction was transferred to a separatory funnel, and diluted with 300 mL of hexane and 50 mL of H$_2$O. The layers were separated, and organic layer was washed with H$_2$O (2×100 mL), brine (100 mL), and dried over mgSO$_4$, filtered, and the hexane and THF removed from the filtrate by rotary evaporation. The resulting residue was chromatographed on silicon gel using hexane as eluant. The eluate was concentrated by rotary evaporation followed by high vacuum to give 0.402 g (26% yield) of biphenyl.

Example 19

Synthesis of 4-phenylthioanisole

A 100 mL of reactor equipped with magnetic stir bar was charged with 140 mg (0.15 mmol) of {[(t-Bu)$_2$P(OH)]$_2$PdCl}$_2$ (from Experiment 7), 2.03 g (10.0 mmol) of 4-bromothioanisole, 1.83 g (15.0 mmol) of PhB(OH)$_2$ and 4.16 g (30.0 mmol) of K$_2$CO$_3$ in 13 mL of DME and 7 mL of H$_2$O. The reaction mixture was refluxed for 12 h until the starting material was completely consumed as judged by TLC. The reaction was cooled to room temperature, transferred to a separatory funnel, and diluted with 300 mL of hexane and 100 mL of H$_2$O. The layers were separated, and organic layer was washed with H$_2$O (2×100 mL), brine (100 mL), and dried over mgSO$_4$, filtered, and solvents removed from the filtrate by rotary evaporation. The resulting residue was chromatographed on silicon gel using hexane as eluant. The eluate was concentrated by rotary evaporation followed by high vacuum to give 1.90 g (95% yield) of 4-phenylthioanisole. It was >95% pure by $^1$H NMR and GC/MS. $^1$H NMR (300 MHz, CDCl$_3$): δ7.47–7.39 (m, 5H), 7.31 (m, 2H), 7.22 (m, 2H), 2.39 (s, 3H) ppm. $^{13}$C NMR (75 MHz, CDCl$_3$): δ140.5, 138.0, 137.6, 128.8, 127.4, 127.1, 126.9, 126.8 ppm.

Example 20

Synthesis of Benzophenone

Method A

A 100 mL of reactor equipped with magnetic stir bar was charged with 56.0 mg (0.06 mmol) of {[(t-Bu)$_2$P(OH)]$_2$PdCl}$_2$ (from Experiment 7), 314 mg (2.0 mmol) of bromobenzene, 268.0 mg (2.2 mmol) of PhB(OH)$_2$ and 830 mg (6.0 mmol) of K$_2$CO$_3$ in 12 mL of 1,4-dioxane. The reaction mixture was flushed with CO (1 atm) and stirred. After the reaction was heated to 80° C. for 4 h under CO (1 atm), the reaction was cooled to room temperature, transferred to a separatory funnel, and diluted with 100 mL of benzene, washed with H$_2$O (2×30 mL), and dried over mgSO$_4$. GC analysis revealed the formation of a mixture of PhBr (41%), Ph-Ph (14%), and Ph-CO-Ph (45%).

Method B A 100 mL of reactor equipped with magnetic stir bar was charged with 56.0 mg (0.06 mmol) of {[(t-Bu)$_2$P(OH)]$_2$PdCl}$_2$, 226 mg (2.0 mmol) of chlorobenzene, 268.0 mg (2.2 mmol) of PhB(OH)$_2$ and 830 mg (6.0 mmol) of K$_2$CO$_3$ in 12 mL of 1,4-dioxane. The reaction mixture was flushed with CO (1 atm) and stirred. After the reaction was heated to 80° C. for 4 h under CO (1 atm), the reaction was cooled to room temperature, transferred to a separatory funnel, and diluted with 100 mL of benzene, washed with H$_2$O (2×30 mL), and dried over mgSO$_4$. GC analysis revealed the formation of a mixture of PhBr (14%), Ph-Ph (19%), and Ph-CO-Ph (68%).

TABLE 3

| Example | Catalyst | Aryl compound | Acid | Product | Yield |
| --- | --- | --- | --- | --- | --- |
| 13A | (Me$_3$C)$_2$PH(O) (in situ) + Pd(OAc)$_2$ | 2-chloroanisole | C$_6$H$_5$B(OH)$_2$ | 2-phenylanisole | 98% |
| 13B | (Me$_3$C)$_2$PH(O) + Pd(OAc)$_2$ | 2-chloroanisole | C$_6$H$_5$B(OH)$_2$ | 2-phenylanisole | 94% |
| 13C | {[(t-Bu)$_2$P(OH)]$_2$PdCl}$_2$ | 2-chloroanisole | PhB(OH)$_2$ | 2-phenylanisole | 90% |
| 14A | (Me$_3$C)$_2$PH(O) (in situ) + Pd(OAc)$_2$ | 3-chloroanisole | C$_6$H$_5$B(OH)$_2$ | 3-phenylanisole | 81% |

TABLE 3-continued

| Example | Catalyst | Aryl compound | Acid | Product | Yield |
|---|---|---|---|---|---|
| 14B | {[(t-Bu)$_2$P(OH)]$_2$PdCl}$_2$ | 3-chloroanisole | PhB(OH)$_2$ | 3-phenylanisole | 94% |
| 15A | (Me$_3$C)$_2$PH(O) (in situ) + Pd(OAc)$_2$ | 4-chlorotuluene | PhB(OH)$_2$ | 4-phenyltoluene | n.a. |
| 15B | (Me$_3$C)$_2$PH(O) + Pd(OAc)$_2$ | 4-chlorotuluene | PhB(OH)$_2$ | 4-phenyltoluene | n.a. |
| 15C | {[(t-Bu)$_2$P(OH)]$_2$PdCl$_2$}$_2$ | chlorobenzene | MeC$_6$H$_4$B(OH)$_2$ | 4-phenyltoluene | 94% |
| 16 | {[(t-Bu)$_2$P(OH)]$_2$PdCl}$_2$ | 4-chloroanisole | PhB(OH)$_2$ | 4-phenylanisole | 53% |
| 17 | {[(t-Bu)$_2$P(OH)]$_2$PdCl$_2$}$_2$ | 4-chlorotuluene | MeC$_6$H$_4$B(OH)$_2$ | 4,4'-dimethybiphenyl | 66% |
| 18A | {[(t-Bu)$_2$P(OH)]$_2$PdCl$_2$}$_2$ | bromobenzene | PhB(OH)$_2$ | biphenyl | 65% |
| 18B | (Me$_3$C)$_2$PH(O) + Ni(COD)$_2$ | chlorobenzene | PhB(OH)$_2$ | biphenyl | 26% |
| 19 | {[(t-Bu)$_2$P(OH)]$_2$PdCl$_2$}$_2$ | 4-bromothioanisole | PhB(OH)$_2$ | 4-phenylthioanisole | 95% |
| 20A | {[(t-Bu)$_2$P(OH)]$_2$PdCl$_2$}$_2$ | bromobenzene | PhB(OH)$_2$ | benzophenone | 45% |
| 20B | {[(t-Bu)$_2$P(OH)]$_2$PdCl$_2$}$_2$ | chlorobenzene | PhB(OH)$_2$ | benzophenone | 68% |

Example 21

In a drybox, 50 mg (0.303 mmol) of (Me$_3$C)$_2$PH(O) from Experiment 2, 83.4 mg (0.303 mmol) of Ni(COD)$_2$ (COD=1,5-cyclooctadiene) and 5.0 mL of THF were loaded into a reactor (100 mL) equipped with a magnetic stir bar. The resulting mixture was stirred at room temperature over 10 min. Next, 1.43 g (10.0 mmol) of 4-chloroanisole was added into the mixture above, followed by adding 15 mL (15.0 mmol, 1.0 M solution in THF) of o-tolylmagnesium chloride, and 15 mL of THF into the reactor. The resulting mixture was stirred at room temperature for 15 h. before the reaction mixture was quenched with 10 mL of H$_2$O. The mixture above was extracted with 3×50 mL of diethyl ether. The combined ether extracts were dried over mgSO$_4$, filtered, and the ether and THF removed from the filtrate by rotary evaporation. The resulting residues were chromatographed on silicon gel using ethyl acetate/hexane (5% volume ratio) as eluant. The eluate was concentrated by rotary evaporation followed by high vacuum to yield 1.85 g (93% yield) of 4-o-tolylanisole. It was >95% pure by $^1$H NMR. $^1$H NMR (500 MHz, CDCl$_3$): δ7.47–7.19 (m, 8H), 4.03 (s, 3H), 2.53 (s, 3H) ppm. $^{13}$C NMR (125 MHz, CDCl$_3$): δ158.5, 141.5, 135.3, 134.3, 130.2, 130.1, 129.8, 126.8, 125.7, 113.4, 55.0, 20.4. ppm.

Example 22

The general procedure from Example 13 was followed using chlorobenzene (1.126 g, 10.0 mmol) and o-tolylmagnesium chloride (15 mL, 15.0 mmol) with Ni(COD)$_2$ (83.4 mg, 0.303 mmol) and (Me$_3$C)$_2$PH(O) (50.0 mg, 0.303 mmol) in 20.0 mL of THF. After 15 h at room temperature, the reaction mixture was quenched with 10 mL of H$_2$O. The mixture above was extracted with 3×50 mL of diethyl ether. The combined ether extracts were dried over mgSO$_4$, filtered, and the ether and THF removed from the filtrate by rotary evaporation. The resulting residues were chromatographed on silicon gel using ethyl acetate/hexane (5% volume ratio) as eluant. The eluate was concentrated by rotary evaporation followed by high vacuum to yield 1.62 g (96% yield) of 2-phenyltoluene. It was >95% pure by $^1$H NMR. $^1$H NMR (500 MHz, CDCl$_3$): δ7.62–7.47 (m, 9H), 2.50 (s, 3H) ppm. $^{13}$C NMR (125 MHz, CDCl$_3$): δ142.0, 141.9, 135.2, 130.3, 129.7, 129.1, 128.0, 127.2, 126.7, 125.7, 20.4. ppm.

Example 23

Synthesis of 2-phenyltoluene

In the drybox, 54.0 mg (0.303 mm) of (Me$_3$C)$_2$PH(S) (from Experiment 18), 83.4 mg (0.303 mm) of Ni(COD)$_2$ and 10.0 mL of THF were loaded into a reactor (20 mL) equipped with a magnetic stir bar. The resulting mixture was stirred at room temperatureover a period of 10 min. After addition of 1.126 g (10.0 mm) of chlorobenzene, the resulting mixture was stirred for 5 min until the catalytic reaction was initiated by dropwise addition of 15 mL (15.0 mm, 1.0 M in THF) of o-tolylmagnesium chloride at room temperature over a period of 5 min. The resulting mixture was stirred at room temperature over 12 h before the reaction was quenched with 10.0 mL of H$_2$O, and the mixture was diluted with 300 mL of Et$_2$O. After separation of organic and aqueous phases, the organic phase was washed with 2×100 mL of H$_2$O, and 100 mL of brine, then dried over mgSO$_4$, filtered and concentrated by rotary evaporation. The crude product was purified by column chromatography on silica gel (100:1-hexane:methyl t-butyl ether) to afford 0.96 g (57% yield) of 2-phenyltoluene.

Example 24

Synthesis of 4-(2-tolyl)anisole

In the drybox, 54.0 mg (0.303 mm) of (Me$_3$C)$_2$PH(S) (from Experiment 18), 83.4 mg (0.303 mm) of Ni(COD)$_2$ and 10.0 mL of THF were loaded into a reactor (20 mL) equipped with a magnetic stir bar. The resulting mixture was stirred at room temperatureover a period of 10 min. After addition of 1.43 g (10.0 mm) of 4-chloroanisol, the resulting mixture was stirred for 5 min until the catalytic reaction was initiated by dropwise addition of 15 mL (15.0 mm, 1.0 M in THF) of o-tolylmagnesium chloride at room temperature over a period of 5 min. The resulting mixture was stirred at room temperature over 12 h before the reaction was quenched with 10.0 mL of H$_2$O, and the mixture was diluted with 300 mL of Et$_2$O. After separation of organic and aqueous phases, the organic phase was washed with 2×100 mL of H$_2$O, and 100 mL of brine, then dried over mgSO$_4$, filtered and concentrated by rotary evaporation. The crude product was purified by column chromatography on silica gel (100:1-hexane:methyl t-butyl ether) to afford 0.90 g (45% yield) of 4-(o-tolyl)anisole.

Example 25

Synthesis of t-butyl Phenyl Sulfide

In the drybox, 133.7 mg (0.75 mm) of (Me$_3$C)$_2$PH(S), 170.0 mg (0.75 mm) of Pd(OAc)$_2$ and 10.0 mL of DMSO were loaded into a reactor (50 mL) equipped with a magnetic stir bar. The resulting mixture was stirred at room temperature for 12 h. Next, 2.0 g (17.7 mm) of chlorobenzene, 1.35 g (15.0 mm) of t-butylthiol, and 2.16 g (22.5 mm) of NaO—tBu were added into the reactor. The resulting mixture was refluxed for 12 h. The reaction mixture was then cooled to room temperature, chromatographed on silicon gel using t-butylmethylether/hexane (1% volume ratio) as eluant. The eluate was concentrated by rotary evaporation followed by high vacuum to yield 812 mg (33% yield) of t-butyl phenyl sulfide. It was >95% pure by $^1$H NMR and GC/MS. $^1$H NMR (500 MHz, CDCl$_3$): δ7.4–7.2 (m, 5H), 1.17 (s, 9H) ppm. $^{13}$C NMR (125 MHz, CDCl$_3$): δ137.4, 132.7, 128.5, 128.3, 45.6, 30.9 ppm. HRMS: Calcd for C$_{10}$H$_{15}$S(M$^+$+H): 167.0894. Found: 167.0888.

Example 26

Synthesis of Diphenyl Sulfide

A 50 mL of reactor equipped with magnetic stir bar was charged with 252 mg (0.27 mmol) of {[(t-Bu)$_2$P(OH)]$_2$PdCl}$_2$, 2.90 g (18.47 mmol) of bromobenzene, 1.98 g (18.0 mmol) of PhSH and 3.46 g (36.0 mmol) of NaO—tBu in 20.0 mL of toluene. The resulting mixture was refluxed for 15 h before the mixture was cooled to room temperature and quenched with 100 mL of H$_2$O. The mixture was transferred to a separatory funnel, and extracted with EtOAc (2×200 mL). The layers were separated, and organic layer was washed with H$_2$O (100 mL), brine (150 mL), and dried over mgSO$_4$, filtered, and the solvents removed from the filtrate by rotary evaporation. The product was isolated by distillation. The final product was obtained as a colorless oil (2.24 g, 66% yield).

Example 27

Synthesis of Diphenyl-p-tolylphosphine

A 100 mL of reactor equipped with magnetic stir bar was charged with 140 mg (0.15 mmol) of {[(t-Bu)$_2$P(OH)]$_2$PdCl}$_2$, 1.27 g (10.0 mmol) of 4-chlorotoluene, and 10.0 mmol of KPPh$_2$ in 30.0 mL of THF. The resulting mixture was refluxed for 17 h before the reaction was cooled to room temperature, quenched with with 20 mL of H$_2$O. The phosphorus-31 NMR spectrum of the reaction mixture at this point showed the δ32.1 [~10%, Ph$_2$PH(O)] and −5.0 (~90%, MeC$_6$H$_4$-PPh$_2$) resonances.

Example 28

Synthesis of Di-tert-Butylphenylphosphine Oxide
Method A

A 20 mL of reactor equipped with magnetic stir bar was charged with 186.0 mg (0.20 mmol) of {[(Me$_2$CH)$_2$P(OH)]$_2$PdCl}$_2$ (from Experiment 13), 1.57 g (10.0 mmol) of bromobenzene, 1.62 g (10.0 mmol) of (t-Bu)2P(H)O and 1.38 g (10.0 mmol) of K$_2$CO$_3$ in 20.0 mL of dioxane. The resulting mixture was refluxed for 24 h before the reaction was cooled to room temperature, quenched with with 5.0 mL of H$_2$O. The phosphorus-31 NMR spectrum of the reaction mixture at this point showed the δ53.2 resonances.

Method B

A 20 mL of reactor equipped with magnetic stir bar was charged with 467.0 mg (0.50 mmol) of {[(Me$_2$CH)$_2$P(OH)]$_2$PdCl}$_2$ (from Experiment 13), 1.57 g (10.0 mmol) of chlorobenzene, 1.95 g (12.0 mmol) of (t-Bu)2P(H)O and 2.76 g (20.0 mmol) of K$_2$CO$_3$ in 20.0 mL of THF. The resulting mixture was refluxed for 15 h before the reaction was cooled to room temperature, quenched with with 5.0 mL of H$_2$O. The phosphorus-31 NMR spectrum of the reaction mixture at this point showed the δ65.1 (~80%) and 51.1 (~15%, Ph(t-Bu)$_2$P(O)) resonances.

TABLE 4

| Ex. | Catalyst | Aryl compound | Acid | Product | Yield |
|---|---|---|---|---|---|
| 21 | (Me$_3$C)$_2$PH(O) + Ni(COD)$_2$ | 4-chloroanisole | o-tolylmagnesium chloride | 4-o-tolylanisole | 93% |
| 22 | (Me$_3$C)$_2$PH(O) + Ni(COD)$_2$ | chlorobenzene | o-tolylmagnesium chloride | 2-phenyltoluene | 96% |
| 23 | (Me$_3$C)$_2$PH(S) + Ni(COD)$_2$ | chlorobenzene | o-tolylmagnesium chloride | 2-phenyltoluene | 57% |
| 24 | (Me$_3$C)$_2$PH(S) + Ni(COD)$_2$ | 4-chloroanisole | o-tolylmagnesium chloride | 4-(o-tolyl)anisole | 45% |
| 25 | (Me$_3$C)$_2$PH(S) + Pd(OAc)$_2$ | chlorobenzene | t-butylthiol | t-butyl phenyl sulfide | 33% |
| 26 | {[(t-Bu)$_2$P(OH)]$_2$PdCl}$_2$ | bromobenzene | phenylthiol | diphenylsulfide | 66% |
| 27 | {[(t-Bu)$_2$P(OH)]$_2$PdCl}$_2$ | 4-chlorotoluene | KPPh$_2$ | MeC$_6$H$_4$-PPh$_2$ | n.a. |
| 28A | {[(Me$_2$CH)$_2$P(OH)]$_2$PdCl}$_2$ | 2-chloroanisole | KPPh$_2$ | Ph$_2$PH | n.a. |
| 28B | {[(Me$_2$CH)$_2$P(OH)]$_2$PdCl}$_2$ | 2-chloroanisole | KPPh$_2$ | Ph$_2$PH | n.a. |

Example 29

Synthesis of 2-Propenoic acid, 3-[4-acetylphenyl]-t-butylester

A 50 mL of reactor equipped with magnetic stir bar was charged with 468 mg (0.50 mmol) of {[(t-Bu)$_2$P(OH)]$_2$PdCl}$_2$, 4-chloroacetophenone (2.58 g, 16.7 mmol), anhydrous tetrabutylammonium bromide (1.07 g, 3.33 mmol) and anhydrous sodium acetate (1.51 g, 18.4 mmol), t-butylacrylate (2.99 g, 23.3 mmol) in 10 mL of DMF. The reaction mixture was vigorously stirred and heated to 135–140° C. for 24 h before the mixture was cooled to room temperature and quenched with 25 mL of H$_2$O. The mixture was transferred to a separatory funnel, and diluted with 300 mL of diethyl ether. The layers were separated, and organic layer was washed with H$_2$O (2×100 mL), brine (100 mL), and dried over mgSO$_4$, filtered, and the solvents removed from the filtrate by rotary evaporation. The product was isolated by bulb-to-bulb distillation. The final product was obtained as a colorless solid (2.73 g, 66% yield).

Example 30

Synthesis of 2-Propenoic acid, 3-[4-phenyl]-t-butylester
Method A

A 50 mL of reactor equipped with magnetic stir bar was charged with 62.2 mg (0.067 mmol) of {[(t-Bu)$_2$P(OH)]$_2$PdCl}$_2$, bromobenzene (2.62 g, 16.7 mmol), anhydrous tetrabutylammonium bromide (1.07 g, 3.33 mmol) and potassium carbonate (2.53 g, 18.3 mmol), t-butylacrylate (2.99 g, 23.3 mmol) in 10 mL of DMF. The reaction mixture was vigorously stirred and heated to 135–140° C. for 24 h before the mixture was cooled to room temperature and quenched with 25 mL of H$_2$O. The mixture was transferred to a separatory funnel, and diluted with 300 mL of CH$_2$Cl$_2$. The layers were separated, and organic layer was washed with H$_2$O (2×100 mL), brine (100 mL), and dried over mgSO$_4$, filtered, and the solvents removed from the filtrate by rotary evaporation. The product was isolated by bulb-to-bulb distillation. The final product was obtained as a colorless oil (2.65 g, 78% yield).

Method B

A 50 mL of reactor equipped with magnetic stir bar was charged with 45.3 mg (0.0667 mmol) of {[(t-Bu)$_2$P(OH)]PdCl$_2$}$_2$, bromobenzene (2.62 g, 16.7 mmol), anhydrous tetrabutylammonium bromide (1.07 g, 3.33 mmol) and potassium carbonate (2.53 g, 18.3 mmol), t-butylacrylate (2.99 g, 23.3 mmol) in 10 mL of DMF. The reaction mixture was vigorously stirred and heated to 135–140° C. for 24 h before the mixture was cooled to room temperature and quenched with 25 mL of H$_2$O. The mixture was transferred to a separatory funnel, and diluted with 300 mL of CH$_2$Cl$_2$. The layers were separated, and organic layer was washed with H$_2$O (2×100 mL), brine (100 mL), and dried over mgSO$_4$, filtered, and the solvents removed from the filtrate by rotary evaporation. The product was isolated by bulb-to-bulb distillation. The final product was obtained as a colorless oil (2.19 g, 64% yield).

What is claimed is:

1. A process to prepare biaryls of the formula $R^1$–$R^7$ comprising contacting a Grignard reagent of the formula $R^7$—MgX with an aryl compound of the formula $R^1$—X in the presence of a catalytic amount of a coordination compound comprising one or more transition metals complexed to a phosphine oxide compound of the formula HP(O)$R^4R^5$ or a phosphine sulfoxide compound of the formula HP(S)$R^4R^5$, wherein X is a halogen;

$R^1$ is an optionally substituted aryl;

$R^7$ is selected from the group consisting of hydrocarbyl, substituted hydrocarbyl, hydrocarbylamino, alkoxy, aryloxy, and heterocyclic; and $R^4$ and $R^5$ are independently selected from the group consisting of hydrocarbyl, substituted hydrocarbyl, heterocyclic, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocyclic, and optionally $R^4$ and $R^5$ can together form a ring.

2. The process of claim 1 wherein $R^1$ is an optionally substituted phenyl.

3. The process of claim 2 wherein the transition metal is selected from Periodic Group VIII.

4. The process of claim 3 wherein $R^4$ and $R^5$ are independently selected from the group consisting of hydrocarbyl, substituted hydrocarbyl and heterocyclic, and wherein the transition metal is Ni.

5. The process of claim 4 wherein $R^7$ is an optionally substituted aryl.

6. The process of claim 5 wherein X is Cl.

7. The process of claim 6 wherein:

$R^1$ is selected from the group consisting of 4-methoxyphenyl and phenyl;

$R^7$ is o-tolyl; and $R^4$ and $R^5$ are t-butyl.

* * * * *